(12) United States Patent
Ford et al.

(10) Patent No.: US 7,356,115 B2
(45) Date of Patent: Apr. 8, 2008

(54) RADIATION SCANNING UNITS INCLUDING A MOVABLE PLATFORM

(75) Inventors: John Ford, Madison, TN (US); Edward J. Seppi, Portola Valley, CA (US)

(73) Assignee: Varian Medical Systems Technology, Inc., Palo Alto, CA (US)

( * ) Notice: Subject to any disclaimer, the term of this patent is extended or adjusted under 35 U.S.C. 154(b) by 210 days.

(21) Appl. No.: 10/310,060

(22) Filed: Dec. 4, 2002

(65) Prior Publication Data

US 2004/0109532 A1 Jun. 10, 2004

(51) Int. Cl.
*G01N 23/04* (2006.01)

(52) U.S. Cl. .............................. 378/57; 378/4

(58) Field of Classification Search ............ 378/57, 378/44–46, 53, 55, 86, 88, 197–198, 38, 378/195–196, 62, 4–20; 250/358.1, 359.1, 250/360.1; 209/576, 589; 414/794.2, 788.7, 414/222.01

See application file for complete search history.

(56) References Cited

U.S. PATENT DOCUMENTS

| | | |
|---|---|---|
| 3,018,374 A | 1/1962 | Pritchett |
| 3,158,744 A | 11/1964 | Bernstein |
| 3,636,353 A | 1/1972 | Untermyer |

(Continued)

FOREIGN PATENT DOCUMENTS

EP 0 816 873 A1 1/1998

(Continued)

OTHER PUBLICATIONS

McDonald, Marci; "Checkpoint Terror Border Searches Snarl the Free Flow of Goods" U.S. News and World Report, p. 52, Feb. 11, 2002.

(Continued)

*Primary Examiner*—Hoon Song
(74) *Attorney, Agent, or Firm*—Brandon N. Sklar; Kaye Scholer LLP

(57) ABSTRACT

A scanning unit for inspecting objects comprises in one embodiment a radiation source to emit a beam of radiation, a rotatable platform to support an object for inspection by the beam of radiation and a detector positioned to receive radiation after interaction of the beam with the object. At least one of the platform, the source and the detector may be moved in a first direction, such as vertically. The object may be scanned while being rotated and moved to generate volumetric computed tomographic images. The rotational and movement of the platform and the object may also be indexed. The beam of radiation may be a horizontally extending cone beam or a fan beam. The detector may extend horizontally, as well. The rotational and/or vertical position of the platform may be used to direct the object along one of multiple exit paths. The scanning unit may provide a vertically extending radiation beam and a vertically extending detector to conduct line scanning. The radiation source may be a source of X-rays, for example. Multiple sources may be provided. The scanning unit may also provide a pencil beam and a movable detector to detect scattered radiation. The pencil beam may induce fission in fissionable material in the object. The source of the pencil beam may be a source of neutrons or gamma rays, for example. Stimulated emissions, such as nuclear resonance fluorescence, may also be detected.

91 Claims, 14 Drawing Sheets

U.S. PATENT DOCUMENTS

| | | | |
|---|---|---|---|
| RE28,544 E | 9/1975 | Stein et al. | |
| 3,924,132 A | 12/1975 | Koslow | |
| 4,031,545 A | 6/1977 | Stein et al. | |
| 4,149,081 A | 4/1979 | Seppi | |
| 4,229,654 A | 10/1980 | Arya et al. | |
| 4,251,726 A | 2/1981 | Alvarez | |
| 4,357,535 A | 11/1982 | Haas | |
| 4,422,177 A * | 12/1983 | Mastronardi et al. | 378/17 |
| 4,430,568 A | 2/1984 | Yoshida et al. | |
| 4,521,900 A | 6/1985 | Rand | |
| 4,599,740 A | 7/1986 | Cable | |
| 4,600,998 A * | 7/1986 | Huet | 702/40 |
| 4,671,256 A | 6/1987 | Lemelson | |
| 4,722,096 A | 1/1988 | Dietrich et al. | |
| 4,769,830 A * | 9/1988 | Peterson et al. | 378/54 |
| 4,824,349 A * | 4/1989 | Oku et al. | 425/29 |
| 4,839,913 A * | 6/1989 | Annis et al. | 378/44 |
| 4,918,315 A | 4/1990 | Gomberg et al. | |
| 4,941,162 A * | 7/1990 | Vartsky et al. | 378/3 |
| 4,956,856 A | 9/1990 | Harding | |
| 4,963,746 A * | 10/1990 | Morgan et al. | 250/363.02 |
| 4,987,584 A | 1/1991 | Doenges | |
| 5,044,002 A | 8/1991 | Stein | |
| 5,065,418 A | 11/1991 | Bermbach et al. | |
| 5,076,993 A | 12/1991 | Sawa et al. | |
| 5,098,640 A | 3/1992 | Gozani et al. | |
| 5,115,459 A | 5/1992 | Bertozzi | |
| 5,124,554 A | 6/1992 | Fowler et al. | |
| 5,153,439 A | 10/1992 | Gozani et al. | |
| 5,164,971 A * | 11/1992 | Peyret et al. | 378/4 |
| 5,175,756 A * | 12/1992 | Pongratz et al. | 378/88 |
| 5,200,626 A | 4/1993 | Schultz et al. | |
| 5,278,418 A | 1/1994 | Broadhurst | |
| 5,293,414 A * | 3/1994 | Ettinger et al. | 378/88 |
| 5,313,511 A | 5/1994 | Annis et al. | |
| 5,323,004 A * | 6/1994 | Ettinger et al. | 250/336.1 |
| 5,367,552 A | 11/1994 | Peschmann | |
| 5,410,156 A * | 4/1995 | Miller | 250/390.04 |
| 5,420,905 A | 5/1995 | Bertozzi | |
| 5,442,672 A * | 8/1995 | Bjorkholm et al. | 378/4 |
| 5,490,218 A | 2/1996 | Krug et al. | |
| 5,491,734 A | 2/1996 | Boyd et al. | |
| 5,493,596 A | 2/1996 | Annis | |
| 5,495,106 A | 2/1996 | Mastny | |
| 5,524,133 A | 6/1996 | Neale et al. | |
| 5,557,108 A | 9/1996 | Tumer | |
| 5,600,303 A * | 2/1997 | Husseiny et al. | 340/568.1 |
| 5,600,700 A | 2/1997 | Krug et al. | |
| 5,611,502 A | 3/1997 | Edlin et al. | |
| 5,638,420 A | 6/1997 | Armistead | |
| 5,642,394 A | 6/1997 | Rothschild | |
| 5,648,996 A * | 7/1997 | Gupta | 378/4 |
| 5,692,028 A | 11/1997 | Geus et al. | |
| 5,692,029 A | 11/1997 | Husseiny et al. | |
| 5,696,806 A | 12/1997 | Grodzins et al. | |
| 5,729,582 A | 3/1998 | Ham et al. | |
| 5,784,430 A | 7/1998 | Sredniawski | |
| 5,818,054 A | 10/1998 | Randers-Pehrson et al. | |
| 5,838,758 A | 11/1998 | Krug et al. | |
| 5,838,759 A | 11/1998 | Armistead | |
| 5,841,832 A | 11/1998 | Mazess et al. | |
| 5,917,880 A | 6/1999 | Bjorkholm | |
| 5,930,326 A | 7/1999 | Rothschild et al. | |
| 5,974,111 A | 10/1999 | Krug et al. | |
| 6,018,562 A | 1/2000 | Willson | |
| 6,078,642 A | 6/2000 | Simanovsky et al. | |
| 6,088,423 A | 7/2000 | Krug et al. | |
| 6,148,058 A * | 11/2000 | Dobbs | 378/19 |
| 6,151,381 A * | 11/2000 | Grodzins et al. | 378/90 |
| 6,198,790 B1 * | 3/2001 | Pflaum | 378/9 |
| 6,218,943 B1 | 4/2001 | Ellenbogen | |
| 6,249,567 B1 | 6/2001 | Rothschild et al. | |
| 6,269,142 B1 | 7/2001 | Smith | |
| 6,278,115 B1 | 8/2001 | Annis et al. | |
| 6,292,533 B1 | 9/2001 | Swift et al. | |
| 6,347,132 B1 | 2/2002 | Annis | |
| 6,358,377 B1 * | 3/2002 | Schloremberg et al. | 204/192.12 |
| 6,408,088 B1 * | 6/2002 | Hu | 382/131 |
| 6,411,674 B1 * | 6/2002 | Oikawa | 378/21 |
| 6,438,201 B1 | 8/2002 | Mazess et al. | |
| 6,553,094 B1 * | 4/2003 | Bernardi et al. | 378/57 |
| 6,567,496 B1 * | 5/2003 | Sychev | 378/57 |
| 6,584,170 B2 * | 6/2003 | Aust et al. | 378/57 |
| 6,619,839 B2 * | 9/2003 | Yoshimura | 378/196 |
| 6,628,745 B1 * | 9/2003 | Annis et al. | 378/21 |
| 6,661,865 B1 * | 12/2003 | Popilock | 378/19 |
| 6,687,328 B2 * | 2/2004 | Bavendiek et al. | 378/58 |
| 6,735,274 B1 * | 5/2004 | Zahavi et al. | 378/15 |
| 6,785,360 B1 * | 8/2004 | Annis | 378/137 |
| 6,827,489 B2 * | 12/2004 | Nicolas et al. | 378/205 |
| 6,898,263 B2 * | 5/2005 | Avinash et al. | 378/4 |
| 2002/0037068 A1 * | 3/2002 | Oikawa | 378/15 |
| 2003/0031300 A1 * | 2/2003 | Cheng | 378/177 |
| 2003/0128807 A1 * | 7/2003 | Kotler et al. | 378/64 |

FOREIGN PATENT DOCUMENTS

| | | |
|---|---|---|
| JP | 2001013090 | 7/2001 |
| WO | WO 96/13839 | 5/1996 |
| WO | WO 01/60258 | 8/2001 |

OTHER PUBLICATIONS

Revkin, Andrew C.; "Possibility Of Using Trucks For Terror Remains Concern"; NYTimes.com; Oct. 20, 2002; p. 1-5; The New York Times Company; New York City, USA.

Grodzins, Lee; Nuclear Techniques For Finding Chemical Explosives In Airport Luggage; Beam Interactions With Materials and Atoms; May 1991; p. 829-833; vol. B56/57, Part II; Elsevier Science Publishers B.V. (North-Holland); Holland.

* cited by examiner

… …

RADIATION SCANNING UNITS INCLUDING A MOVABLE PLATFORM

Radiation scanning of objects to identify contraband and, more particularly, radiation scanning of objects supported and moved by a platform.

BACKGROUND OF THE INVENTION

Radiation is commonly used in the non-invasive inspection of objects such as luggage, bags, briefcases and the like, to identify hidden contraband at airports and public buildings. The contraband may include hidden guns, knives, explosive devices and illegal drugs, for example. One common inspection system is a line scanner, where the object to be inspected is passed between a stationary source of radiation, such as X-ray radiation, and a stationary detector. The radiation is collimated into a fan beam or a pencil beam. Radiation transmitted through the object is attenuated to varying degrees by the contents of the luggage. The attenuation of the radiation is a function of the density of the materials through which the radiation beam passes. The attenuated radiation is detected and radiographic images of the contents of the object are generated for inspection. The images show the shape, size and varying densities of the contents.

To obtain additional information about the contents of the luggage and other objects, detectors may be provided to detect scattered radiation, as described in U.S. Pat. No. 5,642,394, for example. Systems may combine detection of scattered radiation with the detection of transmitted radiation.

Another technique to enhance the information that may be derived about the composition of the contents of an object is to scan the object with radiation beams having two different energy distributions. A ratio of the attenuation detected at two energy levels is indicative of the atomic numbers of the material through which the radiation beam passes. Dual energy systems enable better detection of plastic materials and illegal drugs, for example.

One disadvantage of radiographic imaging is that all items within the object in the path of the radiation beam are superimposed on the image. If there are many items in the object, it may be difficult to distinguish among them. The identification of dangerous items is thereby hampered. In addition, the orientation and shape of the items within the object could affect whether they can be identified on a radiograph. Thin sheets of explosive materials may also be difficult to identify on a radiograph, particularly if they are oriented perpendicular to the scanning beam.

Computed tomography ("CT") enables the reconstruction of the cross-sectional images of the contents of an object, facilitating the identification of the items in the luggage. CT images also provide higher resolution, greater image contrast and greater sensitivity to characteristics of the object being scanned, than radiographs. However, reconstruction of CT images of an object requires a large number of scans of the object at a plurality of angles. Conducting a sufficient number of scans for CT reconstruction is time consuming. Depending on the system used, CT imaging of an entire piece of luggage may be too slow for practical use in screening luggage in airports, for example.

In U.S. Pat. No. 5,362,552 (the '552 patent), a source of X-ray radiation is provided on one side of an inner surface of a rotating module and a detector array is provided on the opposite side. Luggage is moved through the module incrementally. The module rotates to scan the luggage at a plurality of angles, at each incremental position. The inspection speed may be increased by pre-screening with a line-scan. Then, only suspicious regions identified by the pre-screening step are subjected to CT imaging.

U.S. Pat. No. 6,078,642 ("the '642 patent) discloses a CT scanning system for luggage where data processing techniques are used to speed the inspection rate. As in the '552 patent, an X-ray source and a detector array are disposed on opposing sides of a rotating module. The source may emit a pyramidal cone beam of radiation and the detector array may be 2-dimensional. The module rotates as a piece of luggage is continuously moved through the module, providing helical volumetric CT scanning. CT scanning is said to be provided of the entire piece of luggage, without requiring pre-scanning. The source may emit an X-ray beam of two different energy distributions, as well.

U.S. Pat. No. 5,410,156 discloses an explosives detection system for scanning luggage in airports including a neutron radiation source on one side of an object and a two dimensional detector array on the opposite side of the object. The object is supported on a rotatable platform. Rotation of the platform during scanning enables optional tomographic imaging of an object on the platform, to create three dimensional distributions of hydrogen, carbon, nitrogen and oxygen per cubic through the sample. The ratios of these elements are determined for small volume increments of the sample. Neural net methods are used to determine whether a volume increment contains an explosive.

While the smuggling of contraband, such as guns and explosives, onto planes in carry-on bags and in luggage has been a well known, ongoing concern, a less publicized but also serious threat is the smuggling of contraband across borders and by boat in large cargo containers. Only a small proportion of the cargo containers brought to the United States by boat are inspected, for example. "Checkpoint terror", U.S. News and World Report, Feb. 11, 2002, p. 52.

Standard cargo containers are typically 20-50 feet long (6.1-15.2 meters), 8 feet high (2.4 meters) and 6-9 feet wide (1.8-2.7 meters). Air cargo containers, which are used to contain a plurality of pieces of luggage or other cargo to be stored in the body of an airplane, may range in size (length, height, width) from about 35×21×21 inches (0.89×0.53× 0.53 meters) up to about 240×118×96 inches (6.1×3.0×2.4 meters). Large collections of objects, such as many pieces of luggage, may also be supported on a pallet. Pallets, which may have supporting sidewalls, may be of comparable sizes as cargo containers, at least when supporting objects. The term "cargo conveyance" is used to refer to all types of cargo containers and comparably sized pallets (and other such platforms) supporting objects.

In contrast to the size ranges of cargo containers, typical airport scanning systems for carry-on bags have tunnel entrances up to about 0.40×0.60 meters. Scanning systems for checked luggage have travel openings that are only slightly larger. Since only bags that fit through the tunnel may be inspected, such systems cannot be used to inspect cargo containers. The low energies used in typical X-ray luggage and bag scanners, described above, are also too low to penetrate through the much larger cargo containers. In addition, many such systems are too slow to economically inspect larger objects, such as cargo containers.

U.S. Pat. No. 6,292,533 B1 discloses a mobile X-ray inspection system for large objects, such as a cargo container carried by a vehicle, that uses an X-ray source of 450 kV. The source is supported on a truck and a pencil beam is generated to vertically scan the vehicle. Detectors, also supported on the truck or a boom extending from the truck, are provided to detect radiation transmitted through and scattered by the contents of the object. In use, a vehicle to be inspected parks alongside the scanning unit on the truck. The source and detectors are moved horizontally by a translation system within the truck to horizontally scan the vehicle. While having sufficient penetration, use of a pencil beam may be too slow to efficiently scan cargo containers. The scan motion is said to be "exceedingly slow" (⅓-⅙ of a mile per hour).

U.S. Pat. No. 5,917,880 discloses an X-ray inspection apparatus that may be used to inspect cargo containers, that uses X-ray radiation of about 8 MeV collimated into a vertical fan beam to scan a truck carrying the cargo. A first detector array is aligned with the fan beam to detect radiation transmitted through the truck. A second detector array is provided to detect radiation forward scattered through the truck. The truck is moved through the vertical fan beam. Data from both detectors is used to determine the average atomic number of the attenuating material in the truck to identify the material content in the truck. Images indicative of the material content are then prepared. Data provided by the first detector array is also used to form radiographs of the truck. While faster than a pencil beam, a fan beam may still be too slow to efficiently scan large objects at a reasonable rate.

In U.S. Pat. No. 5,638,420, large containers are inspected by a system on a movable frame. A source of a fan beam, a cone beam or a pencil beam of X-ray radiation, such as a linear accelerator with an accelerating potential in the MV range, is mounted on one side of the frame. A detector array is mounted on an opposing side of the frame. The frame may be self-propelled and advances across the length of the container. Radiographic images are generated for analysis by an operator.

Radiographic images of large objects such as cargo containers suffer from the same problems described above with respect to radiographic images of smaller objects such as luggage. U.S. Pat. No. 5,524,133 discloses scanning systems for large objects such as freight in a container or on a vehicle. In one embodiment, two stationary sources of X-ray radiation are provided, each emitting a beam that is collimated into a fan beam. The sources facing adjacent sides of the freight and the fan beams are perpendicular to each other. A stationary detector array is located opposite each source, on opposite sides of the freight, to receive radiation transmitted through the freight. In addition, X-ray radiation beams having two different energies are emitted by each source. One energy is significantly higher than the other. For example, energies of 1 MeV and 5 or 6 MeV may be used. A ratio of the mean number of X-rays detected at each energy level by the detector array as a whole for each slice or by the individual detectors of the array is determined and compared to a look up table to identify a mean atomic number corresponding to the ratio. The material content of the freight is thereby determined. Three dimensional images based on the ratios of mean atomic number may be reconstructed from the data collected by both detector arrays. The patent states that while the images are coarse, they enable the shapes of certain items to be determined. In combination with the determination of the mean atomic number of the materials in those items, suspicious items may be eliminated or flagged for further inspection.

While three dimensional images based on radiographs are an improvement over radiographs themselves, the high resolution, improved image contrast and the ability to distinguish small differences in characteristics of items within an object that are provided by CT scanning would be advantageous in the inspection of cargo containers. The CT scanning units used in airports for luggage and the like discussed above are not readily scaleable to the large sizes required to scan cargo containers. For example, to accommodate most cargo conveyances, the rotating modules of the '552 patent or the '642 patent would need to be greatly enlarged. Such large rotating units, carrying both the sources and the detectors, would be very expensive and would be difficult to operate and maintain.

Despite the various designs for the inspection of large objects such as cargo containers disclosed in the patents discussed above and in other references, much of the inspection of cargo conveyances is done manually, if at all. "Checkpoint terror", U.S. News and World Report, Feb. 11, 2002, p. 52. Practical, efficient, non-intrusive radiation scanners for the inspection of large objects, such as cargo conveyances, are still needed. The ability to perform CT imaging of large objects is needed, as well. Improved radiation scanners for the inspection of smaller objects, such as luggage, including improved CT imaging of smaller objects, are also needed.

SUMMARY OF THE INVENTION

In accordance with one embodiment of the invention, a scanning unit for inspecting objects is disclosed comprising a radiation source to emit a beam of radiation, a rotatable platform to support an object for inspection by the beam of radiation and a detector positioned to receive radiation after interaction of the beam with the object. At least one of the radiation source, the platform and the detector are movable in a first direction. Preferably, the platform is movable in the first direction. More preferably, the first direction is vertical. The radiation beam may be a horizontally diverging beam, such as a fan beam, or a horizontally and vertically diverging beam, such as a cone beam. In the preferred embodiment, the object is scanned as it is rotated and moved in the first direction. Volumetric CT images may be reconstructed of the object whether the platform, the source and/or the detector are movable in the first direction.

The radiation source may be a source of X-ray radiation, for example. Additional radiation sources may be provided and additional detectors may be provided as necessary to accommodate the additional sources. Each source may emit radiation at different energies or a single, multi-energy source may be provided.

In accordance with another embodiment of the invention, a scanning unit for inspecting objects comprises a radiation source to emit a beam of radiation, a movable platform to support an object for inspection by the beam of radiation and a detector positioned to receive radiation after interaction with the object. A first conveyor is provided to convey the object to the platform for scanning. A second conveyor is provided to convey the object from the platform after scanning and a third conveyor is provided to convey the object from the platform after scanning. An object may be selectively directed to one of the second conveyor and the third conveyor based on the position of the platform. A processor may be programmed to move the platform to align the object with the second conveyor if the object passes inspection and to align the object with the third conveyor if the object has not passed inspection, for example. The platform may be rotatably positionable to align the object with one of the second conveyor and the third conveyor. The second conveyor may be at a different vertical level than the third conveyor and the platform may be movable vertically to align an object supported by the platform with one of the second and third conveyors.

In accordance with another embodiment of the invention, a scanning unit for inspecting objects comprises a radiation source to emit a vertical beam of radiation. A rotatable platform is provided to support an object for inspection by the vertical beam. A conveyor on the platform moves the object horizontally. A vertical detector is positioned to be aligned with the vertical beam, to receive radiation after interaction with the object. The vertical beam may be a fan beam, for example. The platform may vertically displaceable and the scanning unit may further comprise a second radiation source to emit a second, horizontal beam of radiation and a second horizontal detector positioned to receive radiation from the interaction of the horizontal beam with the object. The first source and the second source may be the same.

In accordance with another embodiment of the invention, a scanning unit for inspecting objects comprises a radiation source to emit a pencil beam of radiation, a rotatable platform to support an object for inspection by the beam of radiation and a detector positioned to receive radiation after interaction with the object. At least one of the radiation source, the detector and the platform are displaceable in a first direction. The detector may be movable to receive radiation scattered by the object along a predetermined direction. The detector may be supported on a rotatable ring with an axis of rotation transverse to the platform, for example. The detector may be adapted to detect fission byproducts, for example. The radiation source may be a source of one of neutrons or gamma rays, for example. A second radiation source of a horizontal beam of X-ray radiation and a second, horizontally extending detector aligned with the second source to receive radiation after interaction of the horizontal beam with the object, may also be provided. The source of the pencil beam and the source of the horizontally extending beam may be the same.

In accordance with another embodiment, a scanning unit for inspecting objects comprises a radiation source to emit a beam of radiation, a rotatable platform to support an object for inspection by the beam of radiation and a detector positioned to receive stimulated emissions from the object due to interaction of the beam with the object. At least one of the radiation source and the platform are movable in a first direction. The radiation beam may be a pencil beam emitted along a first axis and the stimulated emissions may be nuclear resonance fluorescence. The detector may be positioned to detect nuclear resonance fluorescence emitted substantially perpendicular to the first axis of the pencil beam. A second radiation source may be provided to emit a horizontal beam of radiation and a second detector may be aligned with the second radiation source to receive radiation after interaction of the second beam with the object. In that case, at least one of the second radiation source, the platform and the second detector are movable in the first direction.

In accordance with another embodiment, a scanning unit for inspecting objects comprises a radiation source to emit a beam of radiation and a platform to support an object for inspection by the beam of radiation. The platform is movable in a non-horizontal direction to move an object supported by the platform in a non-horizontal direction. A detector is positioned to receive radiation after interaction of the beam with the object. The radiation source is at least partially rotatable about an axis transverse to the platform. In that way, the source is at least partially rotated about an object supported by the platform. The source may be supported by a gantry at least partially rotatable about the transverse axis. The detector may be supported by the gantry and be at least partially rotated about the transverse axis, as well. The non-horizontal direction may be vertical.

In accordance with another embodiment, a scanning unit for inspecting objects comprises a stationary radiation source to emit a beam of radiation and a platform to support an object for inspection by the beam of radiation. The platform is rotatable about a first axis and displaceable along a second axis. A stationary detector is positioned to receive radiation after interaction of the beam with the object. The first axis and the second axis may be the same axis, which may a vertical axis.

In accordance with another embodiment of the invention, a method of examining contents of an object comprises rotating the object about an axis of rotation, scanning the object with radiation from a radiation source, detecting radiation interacting with the object with a detector and moving at least one of the object, the radiation source and the detector in a first direction. Scanning may be conducted while the object is being rotated and moved, or rotation and movement may be alternated with scanning of the object. Volumetric computed tomography images may be reconstructed based on the detected radiation. Preferably, the first direction is a vertical direction.

The object may be scanned with one or more radiation beams having first and second energy distributions. Volumetric computed tomography images may be reconstructed based on data collected from scanning at the different energy distributions. The images may be fused.

The object may also be moved horizontally and scanned with a vertical beam of radiation. Radiation resulting from the interaction of the vertical beam with the object is detected with a vertical detector. The object may be rotated between vertical scanning and volumetric computed tomographic images reconstructed based on the detected radiation, as well.

The object may be scanned with radiation to induce fission in fissionable material in the object, if present. The fission byproducts are then detected. The object may be scanned with a pencil beam of neutron or gamma ray radiation to induce the radiation.

The object may be conveyed from the platform along one of a plurality of exit paths based at least in part on one of a rotational position and a vertical position of the platform.

Stimulated emissions, such as nuclear resonance fluorescence, may be detected.

In accordance with another embodiment, a method of examining contents of an object comprises rotating the object, scanning the object with radiation continuously for at least part of the rotation of the object and detecting radiation interacting with the object.

In accordance with another embodiment, a method of examining contents of an object comprises rotating the object, scanning the object with X-ray radiation and detecting radiation interacting with the object.

DESCRIPTION OF PREFERRED EMBODIMENTS

Figure 1:
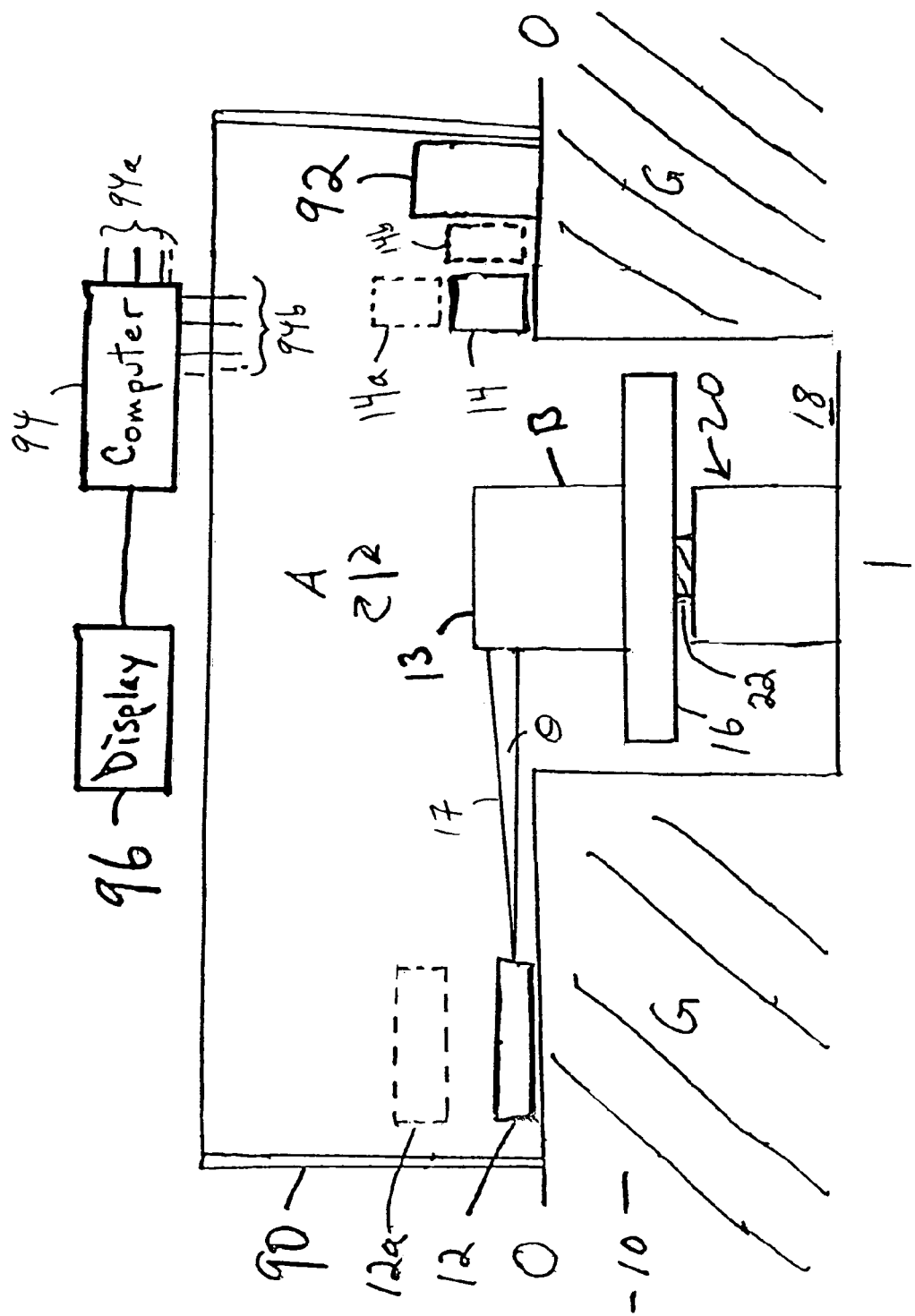
FIG. 1 is a side view of a scanning unit 10 according to one embodiment of the invention, showing a rotatable, vertically displaceable platform in a lowered position.

FIG. 1 is a side view of a scanning unit 10 according to one embodiment of the invention. In this embodiment, the scanning unit 10 comprises a source of radiation 12, such as X-ray radiation, to irradiate an object 13 being scanned, a detector 14 to detect radiation transmitted through the object 13 and a rotating/vertically displaceable platform 16 to support and position the object during scanning. The rotating/vertically displaceable platform 16 is between the source 12 and the detector 14. The source 12, along with suitable collimation, may emit a horizontal beam 17 of radiation and the detector 14 may extend horizontally. The horizontally extending beam may be a cone beam, as shown in FIG. 1, or a fan beam, for example. The object 13 may be a large object, such as a cargo conveyance (cargo container and pallets, for example). The object 13 may also be a smaller object, such as a piece of luggage or a carry-on bag, for example.

In this embodiment, the source 12 and the detector 14 are preferably stationary. It is advantageous to use a stationary source and a stationary detector because the characteristics of those devices may be optimized without being concerned or as concerned about the weight and size of a moving source and/or detector. While preferred, it is not required that the source 12 and the detector 14 be stationary. Examples of non-stationary sources and detectors are discussed in embodiments described below.

Figure 2:
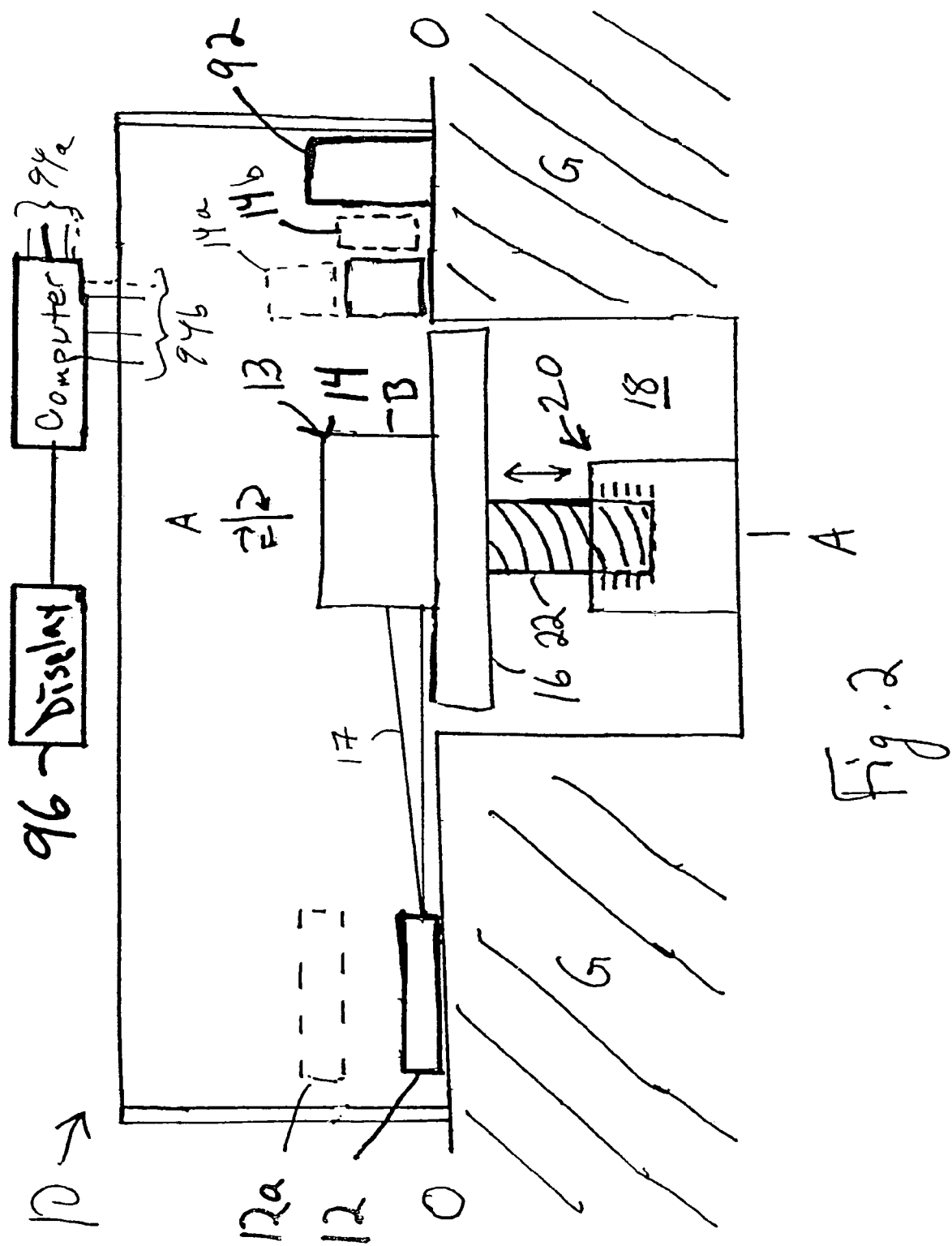
FIG. 2 is a side view of the scanning unit of FIG. 1, wherein the platform is shown in a raised position.

In FIG. 1, the source 12 and the detector 14 are supported at ground level 0. The top of the object 13 extends above ground level. The platform 16 is recessed within a cavity 18. The cavity 18 may be in the ground G. FIG. 2 is a side view of the scanning unit 10 of FIG. 1, wherein the platform 16 is shown in a raised position, at ground level 0. In this embodiment, a conveying system, discussed with respect to FIG. 4a, below, moves the object 13 to the platform 16 along an axis perpendicular to the page.

The platform 16 may be a flat plate. The platform 16 is supported by a mechanical device or system 20 that both rotates the platform about a vertical axis "A" through a center of the plate and moves the platform 16 vertically along the axis. The direction of rotation may be clockwise or counter clockwise when moving vertically in both directions. The direction of rotation may also be clockwise when moving vertically in one direction and counter clockwise when moving vertically in the opposite direction. The mechanical device or system 20 may be one in which the vertical travel of the platform 16, and hence the vertical travel of the object 13 supported by the plate, is a function of the rotation of the platform 16, but that is not required. The speed of movement of the platform 16 is preferably such that the object 13 is stationary with respect to the platform and the contents of the object are stationary with respect to the object as the object is moved. A suitable rate of rotation and vertical movement of the platform 16 may be readily determined by one of skill in the art of radiation and computed tomographic imaging, taking into consideration the packing of the contents of the object 13. An example of movement rates is given below. All or a portion of the platform 16, and any other components of the scanning unit, may be made of material transparent to X-ray or other radiation, if necessary.

The mechanical device 18 may be a screw jack, for example, comprising a threaded post 22 supporting the platform 16, as shown in FIG. 1. The threaded post is received within a threaded cavity of a motor box. Rotation of the post by a motor (not shown) causes rotation of the post. In a basic screw jack, rotation of the screw in one direction raises the platform 16 and rotation in the opposite direction lowers the platform.

The screw jack could also have a double helical groove that switches the direction of the pitch. A ball bearing trapped in the helical groove and a race on the platform 16 oscillates the platform 16 up and down continuously such that the rotation is always in the same direction, as is known in the art.

Figure 3:
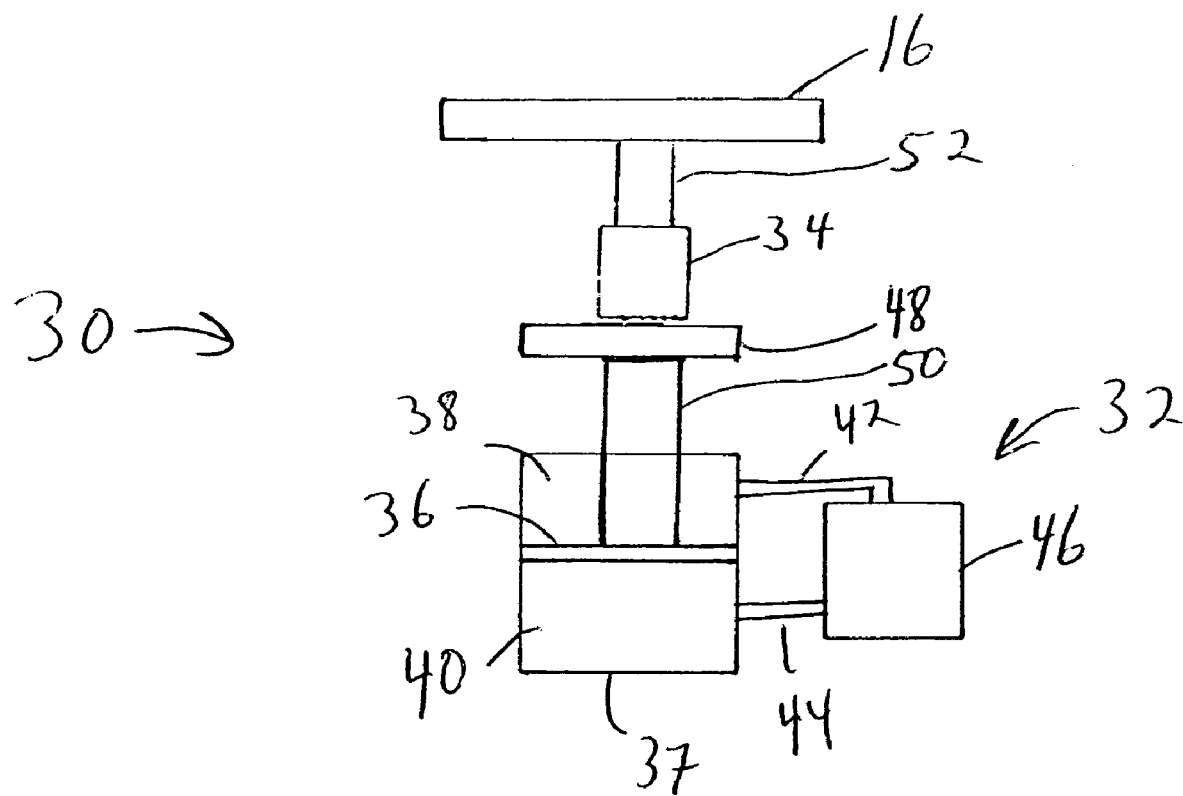
FIG. 3 is another example of a system for rotating and vertically displacing the platform.

FIG. 3 is another example of a system 30 for rotating and vertically displacing the platform 16. The mechanism in FIG. 3 comprises a hydraulic or pneumatic system 32 for moving the platform 16 vertically and a motor 34 for rotating the platform. The hydraulic or pneumatic system 32 comprises a piston 36 within a chamber of a housing 37. The piston divides the chamber into an upper chamber 38 and a lower chamber 40. Driving fluid is provided to and removed from the upper and lower chambers 38, 40 along tubes or pipes 42, 44, respectively, by a pump 46. The piston 36 is connected to a sub-platform 48 through a first rod 50. Movement of the piston 36 within the housing 37 causes the sub-platform 48 to be raised and lowered. The sub-platform 48 supports the motor 34, which is coupled to the platform 16 by a second rod 52. Rotation of the second rod 52 by the motor 34 causes rotation of the platform 16, while vertical movement of the piston 36 and sub-platform 48 causes corresponding vertical movement of the platform. By controlling the rate of rotation of the motor 34 and the rate of vertical movement of the piston 36, the rotational and vertical movements of the platform 16 may be synchronized, if desired.

Other electromechanical, hydraulic and/or pneumatic driving mechanisms may also be used.

Figure 4A:
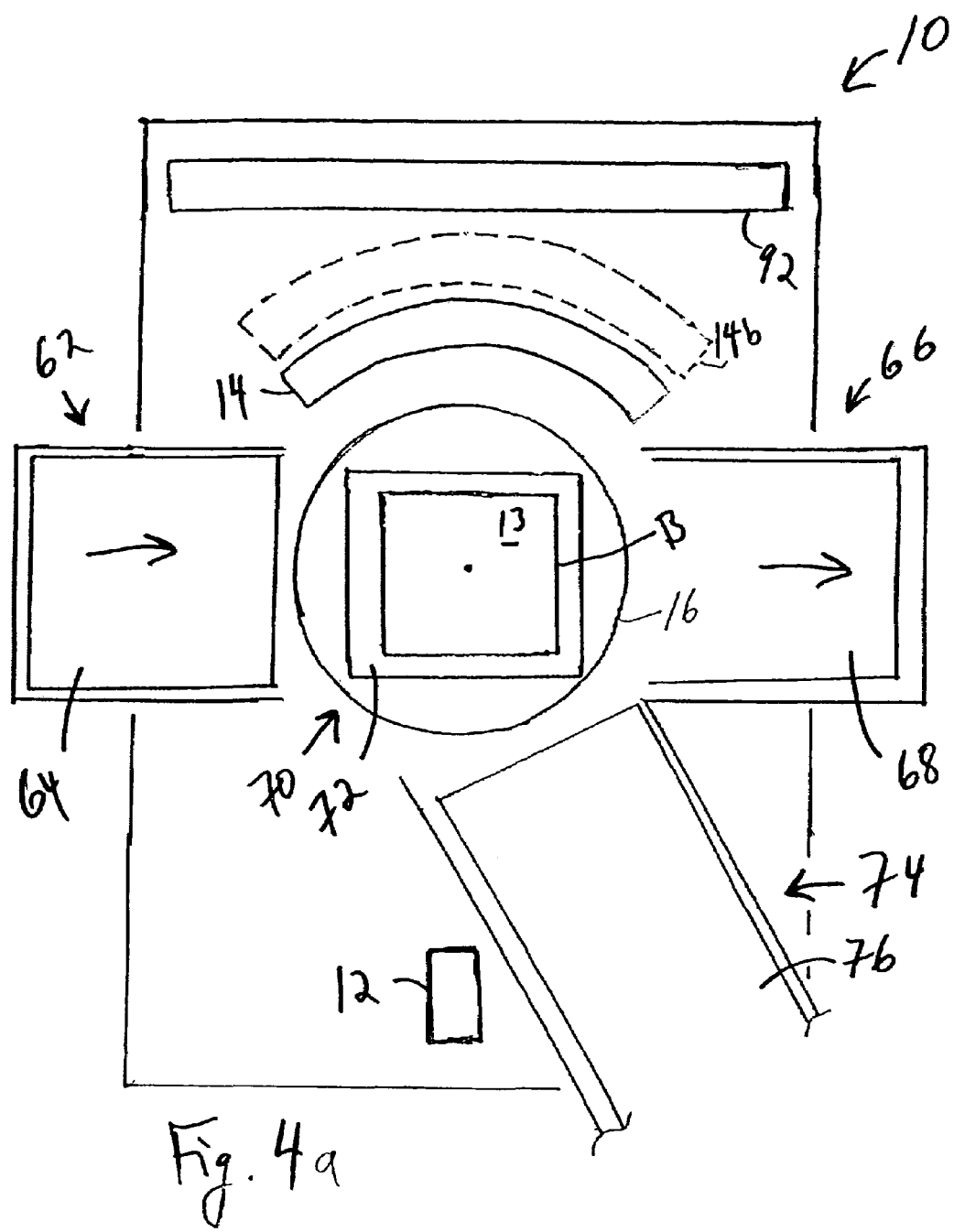
FIG. 4a is a top view of the interior of the scanning unit of the embodiment of FIG. 1.

FIG. 4*a* is a top view of the interior of the scanning unit 10 of the embodiment of FIG. 1. In this example, the platform 16 is circular and is larger than the object 13. The platform 16 may be other shapes and sizes, as well.

A conveyor system may be provided to convey the object 13 to and from the platform 16. The conveyor system comprises a first portion 62 comprising a first conveyor belt 64 that extends from the outside of the scanning unit 10 to the platform 16. A second portion 66 comprises a second conveyor belt 68 extending from the platform 16 to the exterior of the scanning unit 10, providing an exit path for the object 13. A third portion 70 of the conveying system may be provided, comprising a third belt 72 on the platform 16, to convey the object 13 from the first belt and to properly position the object 13 on the platform 16. The third belt 72 also conveys the object 13 to the second belt 68 after scanning is completed. The conveying system may optionally include a fourth portion 74 comprising a fourth conveyor belt 76 to convey suspicious objects along a second exit path from the platform 16, for further inspection, as discussed further below.

An operator may secure the object 13 to the platform 16 when the object is properly positioned with respect to the platform, through ropes, belts and/or clamps, for example, prior to scanning. Automatic systems may be used, as well.

Instead of providing one or two exit paths and associated conveyor belts, the first conveyor belt 64 may be used to both convey the object 13 to the platform 16 and to convey the object 13 from the platform 16. Other devices for conveying objects, such as rotating rollers, may be used instead of conveying belts.

Figure 4B:
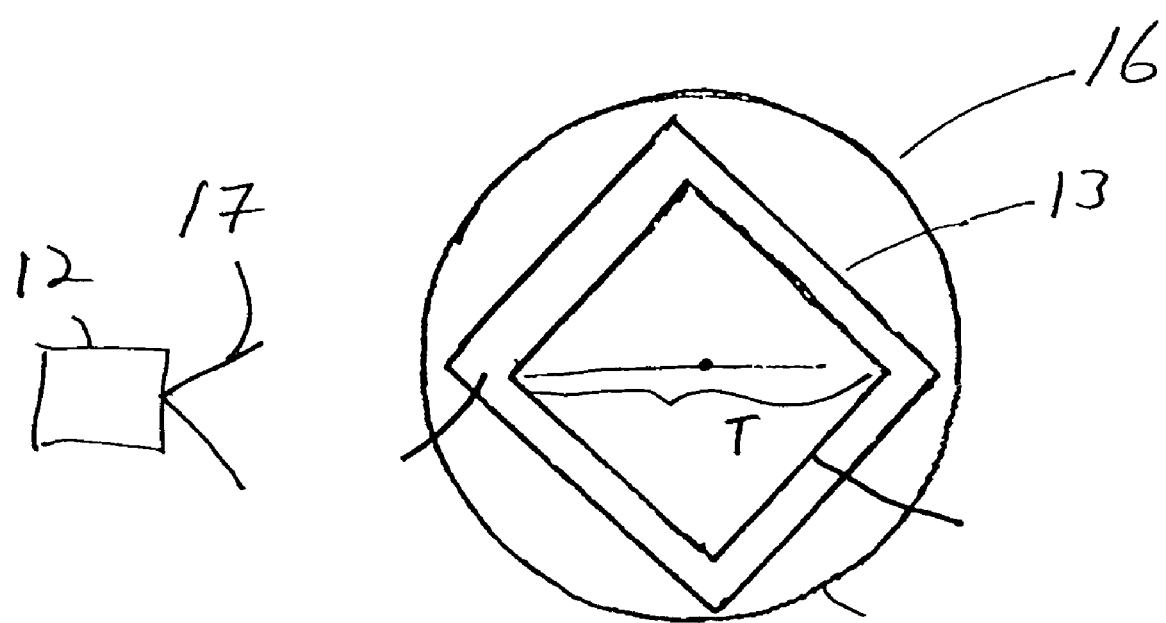
FIG. 4b is a top view of an object on the platform, where the longest thickness of the object during rotation is shown aligned with the radiation beam.

The X-ray source 12 may be a source of bremsstrahlung radiation, for example. The source 12 should generate X-ray radiation with high enough energy to penetrate through the thickness of the object 13 while the object is in any rotational orientation on the platform 16. For example, for X-ray radiation to penetrate through a rectangular cargo conveyance, such as a cargo container or other rectangular object 13 whose largest thickness "T" along the radiation beam 17 during rotation is greater than about 5 feet (1.5 meters), average energies over 1 MeV are preferably used. In a rectangular object 13, the largest thickness T is between opposing corners of the object, as shown in FIG. 4*b*.

Figure 4C:
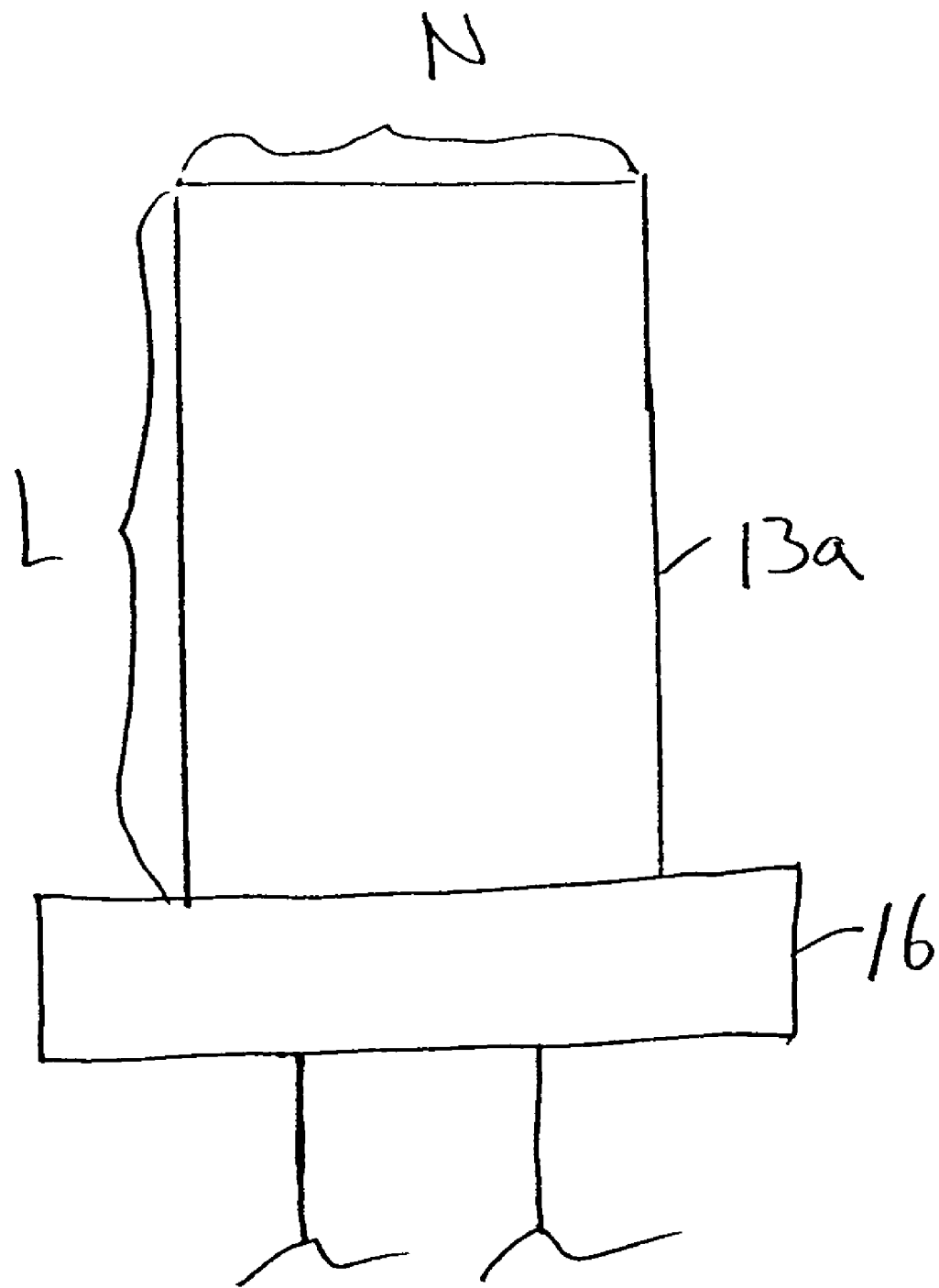
FIG. 4c is a side view of a long object, such as a standard cargo container, on the platform.

To scan long objects, such as a standard cargo container 13*a*, which is about 20 feet long (about 6.1 meters) and about 6-9 feet wide (1.8-2.7 meters), the container may be placed in an upright position on the platform 16, as shown in FIG. 4*c*. The radiation beam would then intercept a diameter through the width "N" of the object, which has much less thickness than the length "L" of the object. A radiation beam with average energy of about 6 MeV or more may be used to scan such a standard cargo container oriented on the platform 16 as shown in FIG. 4*c*. It is noted that depending on the packing and other characteristics of the contents of the cargo container, it might not be practical to place all standard cargo containers in an upright position. X-ray radiation in the KeV range may be used to penetrate through smaller cargo containers and other smaller objects.

If X-ray radiation greater than about 1 MeV is needed to penetrate through the object 13, the X-ray source 12 may be a linear accelerator, such as a Linatron Linear Accelerator ("Linatron®"), having an accelerating potential in a range of about 2 MV or more, available from Varian Medical Systems, Inc., Palo Alto, Calif. ("Varian"), for example. The source may or may not be pulsed. In the Varian Linatron®, 360 pulses are output per second, for example. Other high energy X-ray sources may be used as well, such as electrostatic accelerators, microtrons and betatrons, for example. The X-ray source may also be a radioisotope, such as Cobalt-60, which emits nearly monoenergetic radiation beams. Other sources of monoenergetic radiation may be used, as well. If lower energy X-ray radiation may be used, the source 12 may be an X-ray tube, for example.

Figure 5:
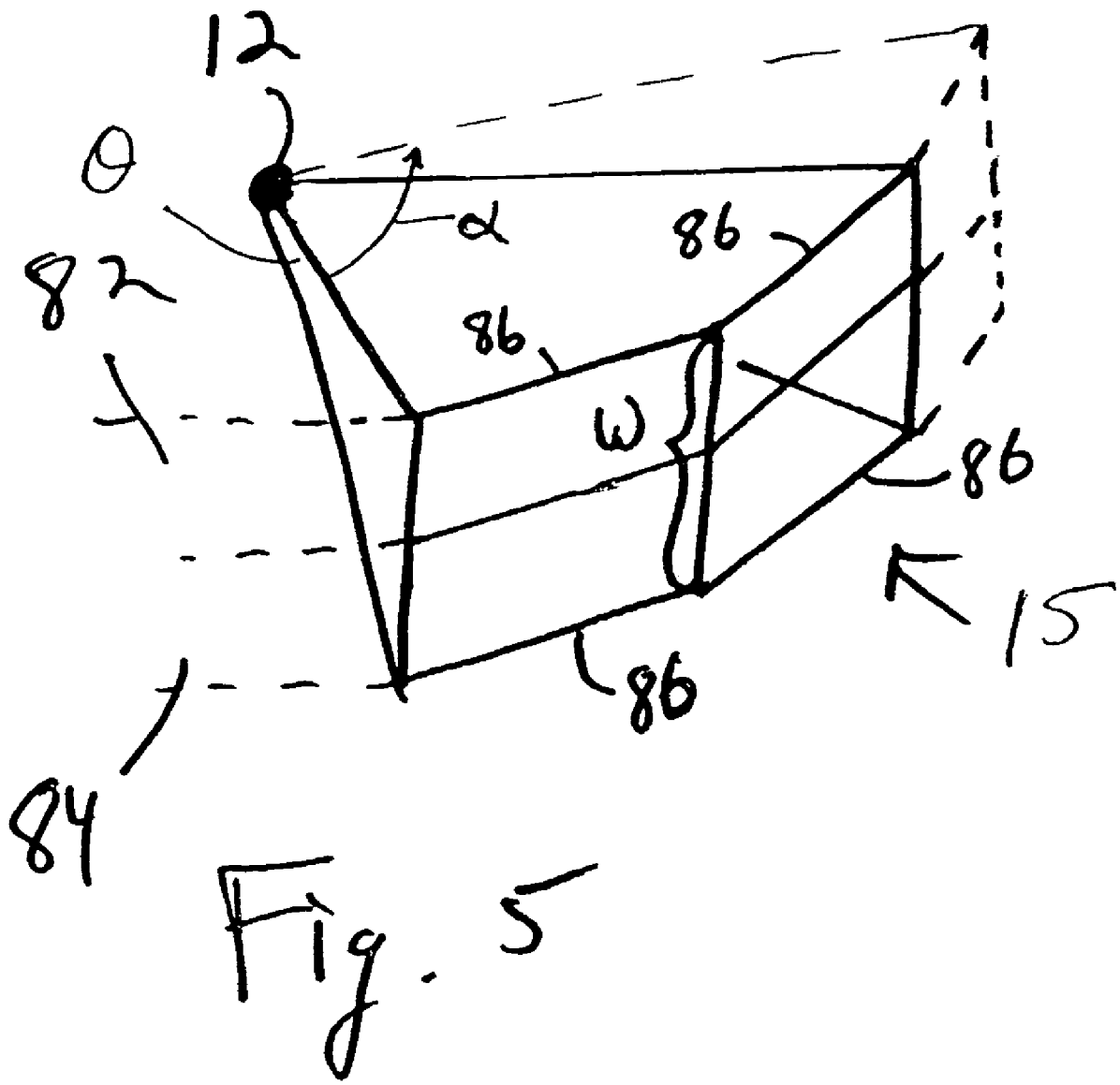
FIG. 5 is a schematic illustration of a portion of a cone beam and a detector array that may be used in the embodiment of FIG. 1.

One or more collimators (not shown) may be provided between the X-ray source 12 and the object 13 to collimate the X-ray beam from each source 12 into a desired shape. The X-ray beam may be collimated into a horizontally diverging beam, such as a cone beam or a fan beam, for example. Here, the term "cone beam" refers to a two dimensional, diverging radiation beam, such as a radiation beam that diverges horizontally and vertically. The cone beam need not be a mathematical cone; it may be an arbitrarily shaped cone with a cross-section having an outer edge with a rectangular, square, circular or elliptical shape, for example. The radiation beam may be a rectangular asymmetric cone beam, for example. FIG. 5 shows a portion of rectangular cone beam 80 intercepting a portion of a two dimensional detector array 15 (discussed further below). If a circular cone beam is used, data collected from semi-circular portions of the circular cone beam proximate the edge of the circle would typically be discarded. The use of a rectangular cone beam instead of a circular cone beam avoids exposure of the object 13 and its contents to this extra radiation that is typically not be used in imaging.

Here, the term "fan beam" refers to a diverging radiation beam having essentially only one dimension, such as a horizontally diverging radiation beam. Since a cone beam covers more volume of the cargo container per unit time than a fan beam, use of a cone beam enables faster scanning than a fan beam. While a fan beam diverges somewhat in a second dimension, the divergence is very small as compared to the divergence in the first dimension, as is known in the art.

The detector 14 may be a spatial detector. The detector 14 may be a detector array 15 comprising a plurality of detector modules, as shown in FIG. 5. When the X-ray radiation is in the form of a cone beam, the detector array may comprise one or more rows of two dimensional detector modules to detect X-ray radiation transmitted through the object 13. In FIG. 5, a portion of two rows 82, 84 of detector modules 86 are shown. The X-ray source 12, shown schematically as a point source in FIG. 5, is aimed at the detector array 15. The object 13 and other components of the scanning unit 10 are not shown in FIG. 5 for ease of illustration. Each two-dimensional detector module 86 comprises a plurality of rows and columns of detector elements, such as photosensitive elements, in a housing. The components of the modules, which are known in the art, are not shown. The photosensitive elements may be photodiodes, for example.

If a fan beam is used, a single row of one dimensional detectors (comprising a single row of detection elements), may be used. Multiple, closely spaced, parallel fan beams may also be defined by one or more collimators. In that case, a row of one dimensional detectors may be provided for each fan beam.

The spatial detector 14 or the detector modules 86 may comprise amorphous Silicon ("aSi") detectors, for example. The detector module 86 may be an aSi detector available from Varian, for example under the trade name PaxScan™

4030. The PaxScan™ 4030 detectors are each 40 cm×30 cm. The detectors may be coupled to signal processing circuitry comprising a preamplifier stage with dynamically controllable signal gain, as described in U.S. application Ser. No. 09/978,727, filed on Oct. 16, 2001, assigned to the assignee of the present invention and incorporated by reference, herein, to improve contrast resolution. The PaxScan™ 4030 may be accompanied by software that enables resolution of about 0.388 mm by mathematically or electronically combining adjacent pixels, referred to as "binning", as is known in the art. "Pixel binning" is discussed in U.S. Pat. No. 5,970,115, for example, which is assigned to the assignee of the present invention and is incorporated by reference herein. Each detector module 86 may be placed end to end, as shown in FIG. 5.

While the detector 14 may have efficiencies of about 1%, higher resolution images may be obtained with higher detector efficiencies. For example, the detectors may have efficiencies of about 10% or greater. 25% to about 75% is preferred. To identify small firearms or other small objects (weighing about 1 pound), for example, the image may have a resolution of from about 0.2 cm to about 0.5 cm. To achieve such resolution in the image, the detector 14 may have pixel spacing of about 0.1 cm or less.

An example of a "deep" detector that may be used in the present invention is described in U.S. application Ser. No. 10/013,199, filed on Nov. 2, 2002, assigned to the assignee of the present invention and incorporated by reference, herein. In addition, the detector may comprise a high spatial density of detector elements. A density of about 60 pixels per square centimeter is preferred for larger objects such as cargo conveyances. A PaxScan 4030™, modified as described in application Ser. No. 10/013,199, may have a density of about 670 pixels per square centimeter, which may be used for smaller objects. Resulting CT and/or radiograph images will have very high resolution.

The longitudinal or axial width (vertical dimension in the embodiment of FIG. 1) of the cone beam 80 at the detector array 15 may approximately correspond to the width "W" of the detector array, as shown in FIG. 5. The cone beam 80 may extend longitudinally (vertically in FIG. 1) over an arc θ of from about 2 degrees to about 30 degrees, for example. The lateral length (horizontal dimensions in the embodiment of FIG. 1) of the cone beam 80 or a fan beam at the location of the object 13 may be slightly greater than the width of the object. In that case, cone beam or fan beam reconstruction algorithms may be used to reconstruct images, as is known in the art. A narrower cone or fan beam may be used, as well. Partial cone or fan beam reconstruction algorithms may be used for radiation beams that do not illuminate the width of the entire object 13, as is also known in the art.

The lateral length of the cone beam 80 (or fan beam) at the detector array 15 may be about the same as the lateral length of the detector array. The cone beam 80 may extend laterally over an arc α of from about 45 degrees to about 80 degrees, for example, depending on the dimensions of the scanning unit 10 and the expected objects to be examined. The detector array 15 may also be shaped like a semi-circular trough or have a dish shaped configuration, as shown in U.S. application Ser. No. 10/202,273, filed on Jul. 24, 2002, assigned to the assignee of the present invention and incorporated by reference, herein. The detector array 15 may be a flat, as well.

Collimators (not shown) may also be provided between the object and the detector array 15 to block scattered radiation from reaching the detectors of the detector array.

Shielding 90 is provided around the scanning unit 10. A variety of shielding configurations and materials may be used, as is known in the art. For example, the shielding may comprise two concentric steel walls, with the space between the walls filled with a radiation absorbing material, such as sand, for example. The shielding material may also comprise blocks of commercially available building materials, such as concrete blocks, which are inexpensive and easy to move. The height of the shielding walls may be more than twice the maximum height of the raised object 13, in the embodiment of FIG. 1, for example. Concrete blocks or slabs may be supported by an I beam support frame extending over the top of the scanning unit 10, as well. The shielding then essentially defines a shielded room including the scanning unit 10. A beam dump 92 of sand or concrete, for example, may be provided behind the detector 14 to reduce shielding requirements, as shown in FIGS. 1 and 4. Detectors may be provided in the beam dump, as well. The source 12 and detector 14 may be provided below ground, at level −1, for example, which may decrease shielding requirements. A shielded tunnel (not shown) may be provided around the source 12, the detector 14, the conveying systems and the platform 16, instead of defining a shielded room, particularly for smaller scanning units.

The detector 14 detects X-ray radiation transmitted through the object 13. The detector 14 is electrically connected to one or more computers 94, which reconstructs the data output by the detector 14 into images, as discussed further below. The computer 94 has one or more inputs 94a to receive the data from the detector 14, and optionally other detectors, also discussed further below. Analog-to-digital converting devices and other electronic components are provided as required. The computer 94 is connected to a display 96 that displays the reconstructed images. The computer 94 may store the reconstructed images in a database, along with identifying information about each object 13, such as the time and date the object was scanned and the source of the object. The scanning unit 10 may include a bar code scanner (not shown) to read the information and provide the information to the computer 94. The operator of the scanning unit 10 can enter the relevant information though a keyboard or the information can be scanned or otherwise entered automatically. For example, a barcode may be applied the object 13 before inspection containing such information. The computer 94 is also connected to the X-ray source 12, to the conveyor system and to the driving mechanism of the platform 16, through outputs 94b, to control their operation (the connections are not shown in FIG. 1 to simplify the illustration). Multiple processors or computers may be used, as well.

During operation of the scanning unit 10 of the embodiment of FIG. 1, an object 13 to be inspected is placed on the first conveyor belt 64. The first conveyor belt 64 and the third conveyor belt 72 (on the platform 16, as shown in FIG. 3) convey the object 13 into position on the platform 16, at ground level 0 (FIG. 1). An operator may then secure the object 13 to the platform 16 by ropes or belts, for example. The X-ray source 12 is activated to emit an X-ray beam collimated into a cone beam 80 of radiation focused on the bottom portion of the object 13. A fan beam may be used, instead. The platform 16 is activated to rotate and recess into the cavity 18 below the platform 16. As the platform 16 rotates and recesses, the cone beam 80 sweeps the object 13 and its contents in a helical pattern. When the platform 16 reaches its lowest level −10, as shown in FIG. 2, the scanning cone beam is at the top of the object 13. The platform 16 then rises (continuing to rotate in the same direction or in the opposite direction, depending on the driving mechanism 20), and continued scanning may optionally be performed.

In one implementation, the distance between the source 12 and the object 13 and the object and the detector 14 may be from about 1.5 to about 2 times the maximum radius of the object. The radiation beam 17 is a cone beam extending longitudinally over an arc θ of about 2 to about 30 degrees, and preferably about 15 degrees. The cone beam 17 may extend laterally over an arc α of about 45 to about 80 degrees. (See FIG. 5). About 45 degrees is preferred. The platform 16 may then be moved in each direction for one minute. The platform 16 may be rotated 2-4 times during movement in one direction, for example. About 300 to about 1,000 projections per each complete rotation of the platform 16 may be taken for CT reconstruction, for example.

The driving mechanism may move the platform 16 vertically a sufficient distance to scan the entire height of the tallest object 13 that can be inspected by the scanning unit 10, or the driving mechanism may be controlled to raise a particular object being scanned the necessary distance. Sensors (not shown) may be provided to identify the height of an object under test and to monitor the rotational and vertical movement of the platform 16. The scanning system 10 may be designed to inspect objects of any height by suitably positioning the source 12 and the detector 14 and providing a driving mechanism that can move the object the necessary distance for complete scanning.

The rotating and vertical motion of the platform 16 may be continuous. Alternatively, the motion may be indexed. For example, if driven by a screw type mechanism, the platform 16 may be rotated and raised in predetermined increments while being scanned. If driven by the driving mechanism in FIG. 3, or another such driving mechanism, the platform 16 may be alternately rotated and raised while being scanned. For example, the platform may be alternately rotated 360 degrees (or slightly more to obtain a complete data set) and raised by a predetermined increment. The rotational and vertical motion of the platform 16 may be synchronized or not.

After the object 13 has been raised and/or lowered a desired amount while being scanned, rotation and vertical motion of the platform 16 is stopped and the source 12 is turned off. The data received by the detector 14, along with the angular and vertical coordinates (cylindrical coordinates) of the platform 16, are provided to the computer 94 and used to reconstruct volumetric computed tomography ("CT") images. As mentioned above, reconstruction algorithms for reconstructing volumetric images based on scanning with a cone beam or a fan beam are known in the art.

Helical volumetric CT scanning may be faster than conventional CT scanning. Objects may therefore be scanned more quickly than in conventional CT systems, with less wear on the source 12. A lower power source may also be used, although scanning with a lower power source may increase scanning times. In either case, source and/or maintenance costs may be reduced. In addition, if a lower power source is used, shielding requirements may be reduced, also reducing costs and the size of the scanning system 10.

Reconstructed images may be analyzed by computer 94 and/or visually by an operator of the system. If desired, the object 13 may be scanned again. When scanning is completed, the object 13 is conveyed from the platform 16. If the object 13 passed inspection, the platform 16 may be aligned with the first exit path along the second conveyor belt 68, as shown in FIG. 4a. The second and third conveyor belts 68, 72 are activated and the object 13 is conveyed off of the platform 16 and out of the scanning unit 10.

If the object 13 did not pass inspection, it may be scanned again on the platform 16. The rotational and vertical movement of the platform 16 is resumed and the source 12 is turned on. The object 13 may be readily scanned as many times as required. Subsequent tests can be conducted at slower rotational and/or vertical movement speeds of the platform 16 or higher dose rates of the X-ray beam 80, than in the initial scan, for the entire object or just while scanning suspicious portions of the object. If the object 13 has been removed from the platform 16 before it is determined that additional scanning is necessary, the second and third conveyor belts 68, 72 may be reversed to return the object 13 to the platform 16.

Repeated scanning of the same object 13 could create a backlog of objects to be inspected. To maintain a high throughput rate through the scanning unit 10, a suspicious object may be directed to the second exit path along the fourth conveyor belt 76, if provided, for temporary storage or to be directed to another site for further inspection. Only suspicious objects would therefore be delayed.

Figure 6:
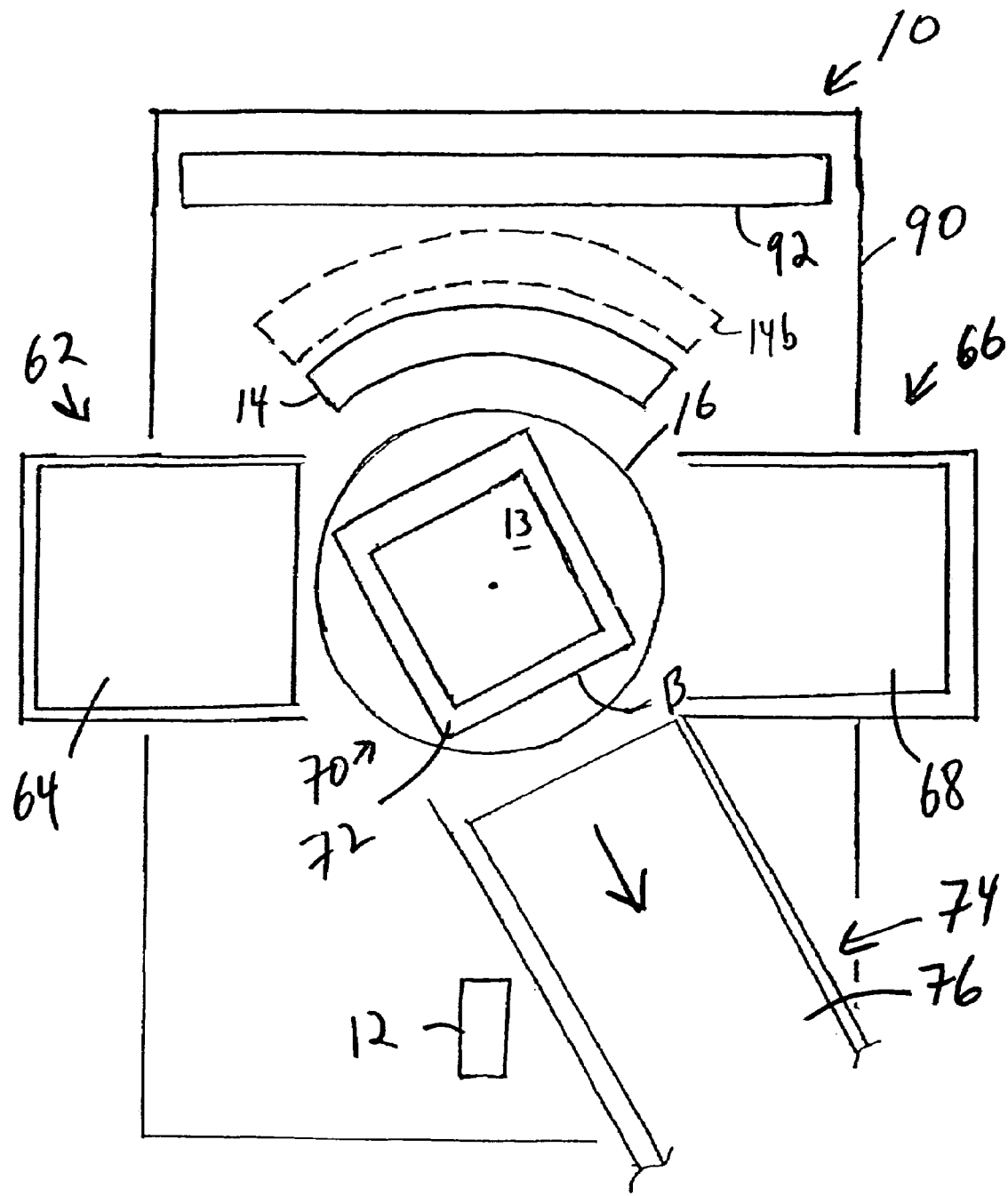
FIG. 6 is a top view of the scanning unit of the embodiment of FIG. 1, where the platform is aligning an object with a second exit path.

The object 13 may be directed to the second exit path by rotating the platform 16 into a position aligned with the fourth conveyor belt 76, as shown in the top view of the scanning unit 10 of FIG. 6. The third and fourth conveyor belts 72, 76 are then activated to convey the object 13 off of the platform 16 and onto the fourth conveyor belt 76.

A suspicious object 13, and other suspicious objects, may be temporarily stored along on the fourth conveyor belt 76 and returned to the platform 16 for subsequent scanning at later time, by reversing the rotation of the second and third conveyor belts. The fourth belt 76 could also lead to a temporary storage area for storage of the object 13 until there is time for rescanning. The fourth conveyor belt 76 may also lead to another scanning station that may be more sensitive to at least certain types of contraband (but possibly slower). The other scanning station may be part of the scanning unit 10 or part of another scanning unit. In the latter case, the fourth conveyor belt 76 may lead directly into the other scanning unit 10. The fourth conveyor belt 76 may also lead to another room or station for manual inspection. The system may be configured to include all these options. Selection of an option may be determined by the computer 94 under program control, by the operator, or both, based on analysis of the reconstructed images of the object 13.

Since the platform 16 is rotatable, the original orientation of the object 13 may be maintained, regardless of the path chosen. Here, for example, the leading edge "B" of the object 13 is the same whether it is conveyed along the first or second exit paths. It is advantageous to maintain the orientation of the object 13 during subsequent scanning on the platform 16 or by another scanning station, to facilitate comparison of images. If it is desired to change the orientation of the object 13 in subsequent imaging, however, that may readily be performed by rotation of the platform 16, as well.

A cavity in the ground need not be provided to accommodate movement of the platform and the source, detector and conveyor system need not be at ground level, as in FIG. 1. In the scanning unit 100 of FIG. 7, for example, entrance and exit portions 102, 104 of a conveyor system are at a level above ground level, such as at level +10 units. A platform 106 has an upper surface 106a that is also at level +10 units when the platform is in a lower, initial position. An object 108 is supported on the upper surface 106a of the platform 106. In this example, the object 108 has a height of +5 units.

It is understood that the object 108 may have other heights. The relative locations of the components of the system and/or the movement of the platform 126 may be modified to accommodate objects of other sizes.

In this embodiment, a source 110 and a detector (not shown in this view but aligned with the source and the object 108 to receive radiation transmitted through the object) are at a level at or above the height of the object 108 when the platform 106 is in its initial, lower position, such as at level +16 units. The platform 106 is coupled to a mechanism 110, such as any of the mechanisms discussed above, or other such mechanisms, to cause rotation and vertical movement of the platform. Here, the conveying system comprises rollers 112. A conveying belt may be used instead, as discussed above.

Figure 7:
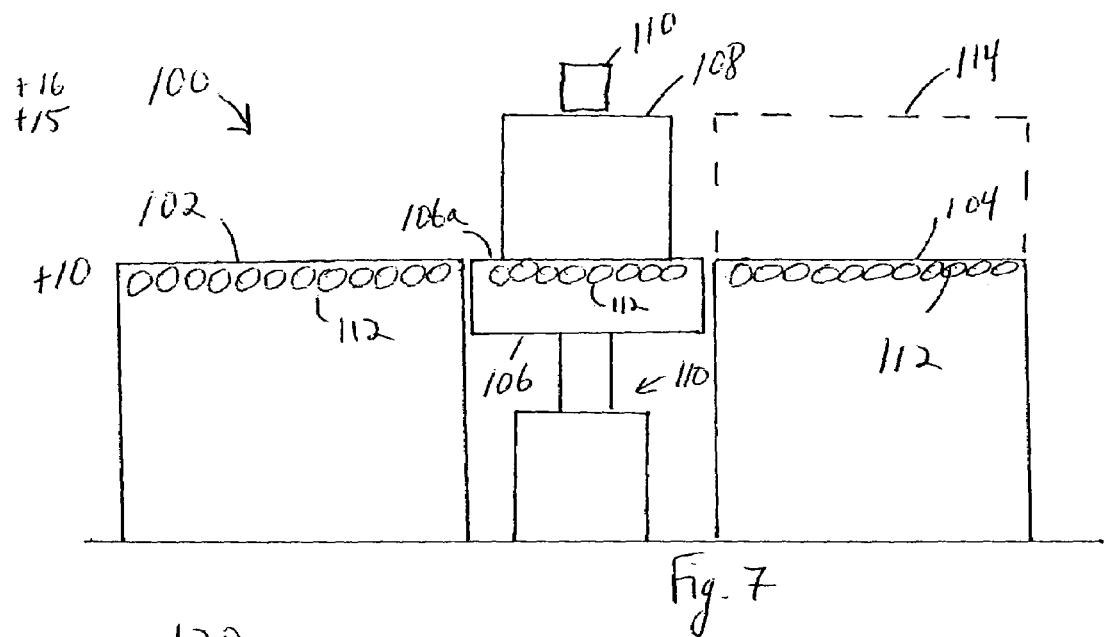
FIG. 7 and FIG. 8 are side views of scanning units in accordance with embodiments of the present invention, showing different arrangements of the source and the conveying system.

In operation, the object 108 is conveyed to the platform 106 while the platform is in the initial position shown in FIG. 7. The platform is then raised to an upper position where the upper surface 106a is at about level +15, for example, while being rotated, so that the entire object 108 may be scanned by an X-ray beam emitted by the source 110. The final position of the upper surface 106a is such that the entire height of the object 108 is scanned, and therefore depends on the dimensions of the scanning radiation beam and the distance from the object to the source 110. As above, the radiation beam may be a cone beam or a fan beam. Also as discussed above, the object 108 may be scanned while being lowered back to its initial position at level +10, as well. When the scanning is completed, the object 108 is conveyed from the platform 106 to the exit portion 104 of the conveying system, and out of the scanning unit 100. Here, the conveying system comprises rollers 112. A conveying belt may be used instead, as discussed above.

An alternative or additional upper exit portion 114 of the conveying system is shown in phantom above the first exit portion 104 of the conveying system, at level +15, for example, to provide an alternative or additional exit path from the scanning unit 100. Depending on the environment of the scanning system, it may be advantageous or necessary for the exit portion of the conveyor system to be at a higher level than the entrance portion 102. In that case, the upper portion 112 of the conveying system would be provided instead of the lower exit portion 104. The upper portion 112 may also serve as an exit path for suspicious objects while the first, lower exit portion 104 may serve as an exit path for objects passing inspection, or vice-a-versa. In this embodiment, the vertical motion of the platform 106 enables sorting of the suspicious and acceptable objects. The upper portion 114 need not be aligned with the first portion 102 of the conveying system. In that case, the rotational orientation of the platform 106 would be aligned with the direction of the upper exit portion 114 when an object is to be conveyed along the upper portion.

Figure 8:
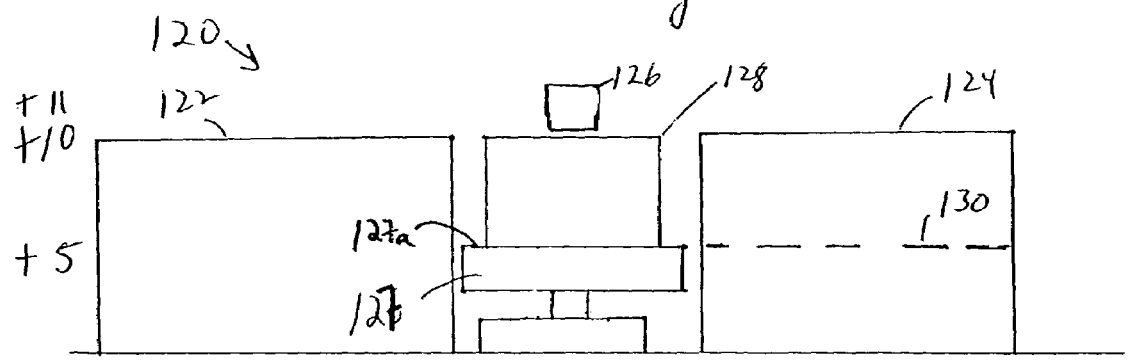

In another configuration of a scanning unit 120 in accordance with an embodiment of the invention shown in FIG. 8, entrance and exit portions 122, 124 of the conveyor system are above ground level and a source 126 is at about the same level as the entrance and exit portions. A platform 127 has a supporting surface 127a supporting an object 128. The platform 127 has an initial, upper position at the same level as the entrance and exit portions 122, 124 and a lower position, shown in FIG. 8. As above, the height of the source depends on the dimensions of the scanning radiation beam and the distance between the source and the object. In this example, the entrance and exit portions 122, 124 are at level +10 units, the source is at level +11 units, the object has a height of +5 units and the upper surface 127a of the platform 127 is at level +5 when the platform is in the lower position. As above, the object 128 may have other heights.

In operation, the upper surface 127a of the platform 127 is initially in the upper position at level +10 units to receive an object 128 from the entrance portion 122. The platform 127 is moved to a lower position at level +5 units, shown in FIG. 8, while being rotated, to expose the entire object 128 to a radiation beam emitted by the source 126. The platform 126 may be rotated and the object 128 scanned while the platform is returned to the upper position, as well. The object 128 may be removed from the platform 126 at level +10, along the second portion 124 of the conveying system. The relative locations of the components of the system and/or the movement of the platform 126 may be modified to accommodate other objects of other sizes.

In this configuration, an alternative or additional lower exit portion 130 of the conveying system is shown in phantom below the first, upper exit portion 124 of the conveying system, at level +5 in this example, as required or desired. The lower exit portion 130 may serve as an exit path for suspicious objects while the upper exit portion 124 may serve as an exit path for objects passing inspection, or vice-a-versa. As in the configuration of FIG. 7, vertical motion of the platform 126 may therefore enable sorting of the suspicious and acceptable objects. Also as above, the lower portion 130 need not be aligned with the first portion 122 of the conveying system and the rotational orientation of the platform 126 may be aligned with the direction of the lower portion when an object is to be conveyed along the lower portion.

Additional information useful in identifying contraband may also be obtained by selectively detecting transmitted energy in different energy ranges. Filters (not shown) may be selectively provided in front of the detector 14 (see FIG. 1) to improve the energy sensitivity of the detector for a particular energy range. For example, the filters may be configured to block radiation transmitted through the cargo below a certain threshold. An example of a detector that is sensitive over a broad energy range and may be used in the present invention is described in U.S. application Ser. No. 10/013,199, filed on Nov. 2, 2002, assigned to the assignee of the present invention and incorporated by reference, herein. Commercially available scintillation based detectors comprising photomultipliers, semiconductor based detectors and gas ionization based detectors sensitive to particular energy ranges may also be used.

As is known in the art, the interaction of X-ray radiation with different materials, including contraband such as explosives, is dependent in part on the energy of the X-ray radiation. Additional information useful in identifying contraband may therefore also be obtained by scanning the object 13 with two or more different energy distributions. One of the energy distributions may be one with an average energy in which the primary interaction of the X-ray radiation with the object is Compton scattering. The other energy distributions may have progressively higher average energies that will cause progressively more pair production and less Compton scattering.

For example, when examining larger objects (having a diameter greater than about 5 feet (about 1.5 meters)), two energy distributions may be provided by X-ray sources with accelerating potentials of 4 MV and 10 MV, or 6 MV and 18 MV or higher, for example. At peak energies of 4 MeV and 6 MeV, the X-ray radiation will predominantly cause Compton scattering. Pair production will only be a small fraction of resulting X-ray interaction. At peak energies of 10 MeV or 18 MeV or higher, more pair production is induced. Compton scattering takes place as well.

For smaller objects, such as luggage, X-ray tubes having accelerating potentials of about 200 KV and 90 KV, for example, may be used to generate X-ray radiation having peak energies of 200 KeV and 90 KeV, respectively. The higher peak energy induces more Compton scattering while the lower peak energy induces more radiation by the photoelectric effect, as is known in the art.

Different X-ray sources emitting X-ray radiation with different peak energies may be used. Corresponding detectors aligned with each source may be provided, as well. In FIG. 1, for example, a second source 12*a* is shown in phantom. A second detector 14*a* is also shown in phantom aligned with the source 12*a* and the object 13. The first and second sources 12, 12*a* and the first and second detectors 14, 14*a* may be stacked, as shown in FIG. 1. The radiation may be emitted by each source 12, 12*a* in alternating pulses, to reduce interference due to scatter. One or more pairs of sources and detectors may also be diametrically arranged around the platform 16. A source/detector pair may be arranged along a diameter perpendicular to, or at another large angle with respect to, to the diameter defined by the source 12 and detector 14 in FIG. 1, to reduce cross talk and interference. For example, a second source/detector pair may be provided along an axis of the first and second conveyor belts 64, 68. The additional source/detector pair may be positioned high enough above the level of the conveyor belts 64, 68 that the object may be conveyed along the belts. The platform 16 may be raised to a sufficient height to be scanned by all of the sources provided. Instead of providing additional detectors aligned with each source, a single detector or detector array could be moved into alignment with an active source.

The additional sources may be linear accelerators and/or X-ray tubes emitting radiation at different peak energies. The additional sources may also include one or more radioisotopes. For example, one of the sources may be Cobalt-60, which emits essentially monoenergetic radiation at multiple energy levels. The second source 12*a* may also be a source of another type of radiation, such as a source of neutrons. Since different types of radiation may interact differently with certain materials, use of a different type of radiation to examine the object 13 may provide additional information that may be useful in identifying the contents of the object.

Alternatively, the source 12 may be capable of selectively emitting X-ray radiation at two or more different energy distributions. Linear accelerators that can emit X-ray radiation at two or more different energy distributions are described in U.S. Pat. No. 6,366,021 B1, U.S. Pat. No. 4,382,208 and U.S. Pat. No. 4,400,650, for example, which are assigned to the assignee of the present invention and are incorporated by reference, herein. If it is desired to use more than two energy distributions, the platform 16 may be raised and lowered multiple times. The object 13 may also be illuminated by multiple energies from a single source 12 by selectively moving an energy selective filter between the source and the object.

One energy distribution may be emitted while the platform is moving in one vertical direction and the other energy distribution may be emitted while the platform is moving in the opposite vertical direction. A pause may be provided in the motion of the platform 16 before changing vertical direction, while the energy is being changed. While concerns over induced radioactivity might limit the upper range of the highest peak energy used to about 20 MeV, it may still be desirable to use higher energies in small area interrogation. For example, if a suspicious region is identified at a lower energy, a higher energy may be used to scan the suspicious region.

Figure 10:
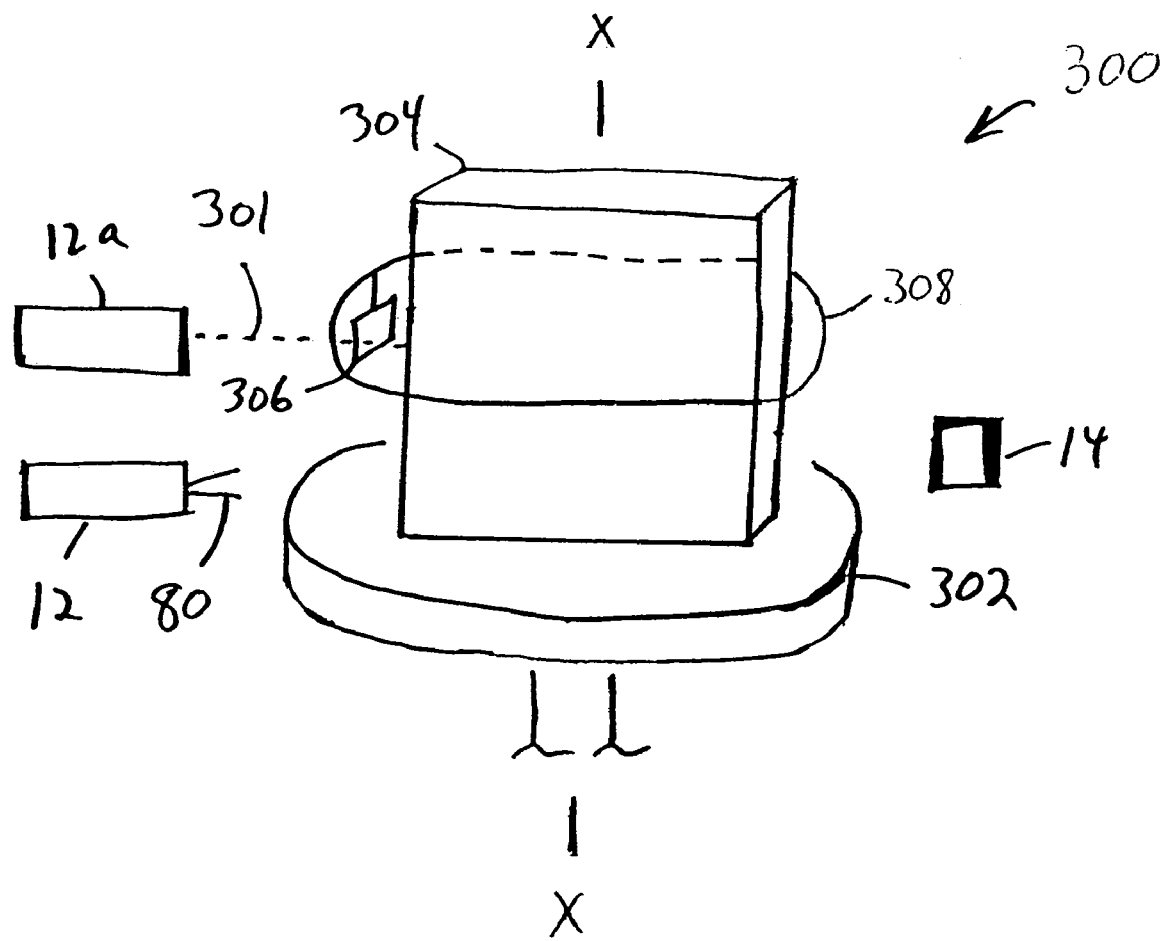
FIG. 10 is a schematic representation of a portion of a scanning unit including a source of a pencil beam of radiation and a movable detector, in accordance with another embodiment.

A plurality of detectors may also be provided in a plurality of locations around the platform 16 to detect scattered radiation. Particular scattering angles may have greater sensitivity to certain types of materials. A single detector may also be provided on a rotating ring surrounding the object, as shown in FIG. 10 to selectively detect radiation scattered at a particular angle, as discussed below.

As mentioned above, the detector of FIG. 1 may be a spatial detector that detects the radiation transmitted through the object 13 at each energy distribution. Alternatively, an energy sensitive detector 14*b* may be provided behind the spatial detector, as shown in phantom in FIGS. 1, 2, 4 and 6. The second, energy sensitive detector 14*b* may be a detector array. When the radiation beam is in the form of a cone beam, the detector 14*b* may comprise one or more rows of two dimensional energy sensitive detectors, in the form of detector modules. The second detector 14*b* may be responsive to the higher energy X-ray radiation transmitted through the object 13 and through the first detector 14. Preferably, the first detector 14 has an efficiency up to about 50%, so that a sufficient amount of X-ray energy will pass through the first detector to be detected by the second detector. The first detector 14 may have higher efficiencies and still allow sufficient X-ray energy to pass through, as well.

Instead of providing a separate energy sensitive detector array 14*b*, two dimensional energy sensitive detectors in the form of detector modules, for example, may also be provided among the two dimensional detectors of the first detector array 15. Filters may be provided between the detectors 14, 14*b* to remove radiation below a certain threshold, to improve the sensitivity of the energy sensitive detector array to higher energies, if desired.

The detectors of the second detector array 14*b* may each comprise scintillators coupled to a photomultiplier tube, for example, as is known in the art. X-ray photons impinging upon the scintillator cause the emission of light photons with energies proportional to the energy of the detected X-ray photons. The light photons are detected by the photomultiplier tube, whose output is proportional to the energy of the detected light photons. Pulse Height Analysis ("PHA") may be used to analyze the data from the energy sensitive detectors. The scintillator may be a cesium iodide scintillator, for example.

Images may be prepared based on data collected at each peak energy. Separate data points may be derived from scanning at each respective energy distribution, for each voxel of the object 13. Data points derived from scanning at the lower energies will be primarily based on the effects of Compton scattering, which is dependent on the atomic number Z of the material (or materials) in the voxel. Data points derived from scanning at the higher energies will be based on pair production, which is dependant on $Z^2$, as well as Compton scattering, to varying degrees. When the object is separately scanned with radiation having more than two energy distributions, some of the information obtained at one energy is correlated to the information obtained at the other. However, the additional information may still be statistically significant. Image contrast may be improved, as well.

Separate images may be reconstructed based on the scans at each energy level. The images may be compared visually or by the computer 94. The data points in all or some of the voxels of the object at each energy may also be compared or processed to derive information indicative of the material content of the portion of the object corresponding to that voxel. Different algorithms may be more sensitive to different physical characteristics of the material content of the voxels. For example, one data point for a voxel may be added to or subtracted from another data point for that voxel. Alternatively, or in addition, a ratio of two data points at each voxel may be computed. The ratio is a value dependent on the average Z and average $Z^2$ of the material in the voxel. Other linear and polynomial combinations of the data points may also be used. The resulting values may be compared by the computer 94 to a database corresponding ratios with materials to identify the material in the voxel. U.S. Pat. No. 4,149,081, for example, discusses the analysis and viewing of data sets derived from different energy levels, in a manner generally applicable here. U.S. Pat. No. 4,194,081 is assigned to the assignee of the present invention and is incorporated by reference herein.

The data points for each voxel are also dependent on the density of the material corresponding to the voxel. The total density of the material may be useful in identifying contraband (explosives, nuclear material and illegal drugs, for example). However, the density of the material may be readily modified by mixing in fillers of different densities, without changing the deleterious characteristics of the contraband. The change in density may make a dangerous explosive appear like an innocuous material on a radiograph. The value of the ratio (average Z/average $Z^2$), however, is independent of the density, making it harder to subvert the system. As mentioned above, other mathematical combinations of the values may be useful, as well, as is known in the art.

The images derived from the second, energy sensitive detector 14b, while providing material content information, have low resolution. Corresponding volumetric CT images derived from data collected by the first detector 14, which have high resolution, may be fused, voxel by voxel, with the images derived from data from the second detector 14b, to yield an image with high spatial resolution that also indicates the material content of the voxel. The position, size and shape of suspicious material, as well as the identity of the material, may then be analyzed visually or by the computer 94.

The computer 94 may implement software programs that automatically analyze the images or the image data to identify suspicious objects or materials, as is known in the art. Software may also be used to enhance the displayed image to facilitate visual analysis by an operator. For example, edge enhancement programs may be used, color may be added to identify certain types of materials and surface rendering may be provided, to make objects more recognizable, as is known in the art.

To scan both large and small objects with the same scanning unit 10, one or more linear accelerators may be provided in a scanning unit to emit radiation beams with average energies greater than about 1 MeV to scan objects whose largest thickness is about 5 feet (about 1.5 meters) or greater, and one or more X-ray tubes may also be provided to scan smaller objects. For scanning smaller objects, such as luggage, X-ray tubes with emitting radiation with peak energies of from about 90 KeV to about 200 KeV may be used, for example. The sources may be selected by an operator of the system based on the size of the objects. If sensors are provided to measure the size of the object, the system may automatically select the sources.

Instead of or along with reconstructing CT images, laminar tomography can also be conducted with the systems of the present invention to reconstruct images of laminar planes of the object 13. Fewer projections are required than in CT reconstruction. For example, laminar planes can be reconstructed based on about 20 to about 30 projections, each separated by one degree of rotation, for example. Laminar reconstruction may therefore be faster than CT reconstruction. The resolution of the images may not be as good as CT, but is better than conventional radiographs. Laminar reconstruction algorithms are known in the art. In one implementation, laminar tomography may be conducted on an entire object 13 by a system of the present invention by scanning planes of the object 13 by rotating the platform 16 and incrementally moving the platform vertically. CT may then be conducted by the system on suspicious regions of the object 13, if any. In another implementation, CT or some other analysis may be conducted on the suspicious region by another scanning unit of any type. Manual inspection may also be performed on suspicious regions. It may also be desirable to conduct CT, another analysis or hand inspection of an entire object that shows suspicious regions.

Figure 9:
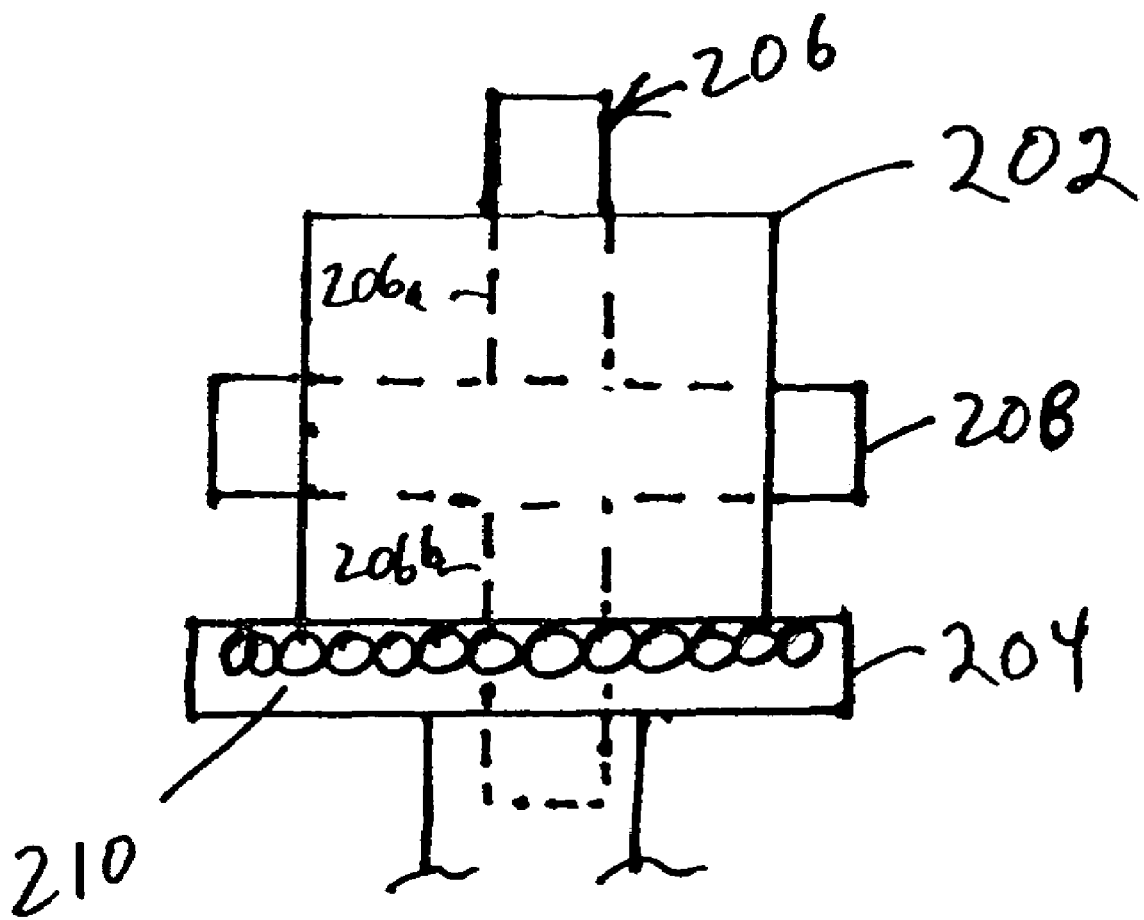
FIG. 9 is a front view of an object on top of a platform, with a vertical line detector for vertical line scanning intersecting a horizontal, spatial detector for volumetric CT imaging, in accordance with another embodiment.

Conventional planar transmission radiography may also be performed along with or instead of volumetric CT imaging, by providing a vertical line detector, as shown in FIG. 9. FIG. 9 is a front view of an object 202 on top of a platform 204, with a vertical line detector 206 intersecting a two dimensional, horizontal spatial detector 208 (for volumetric CT imaging based on a cone beam of radiation). The portions of the vertical line detector 206 and the horizontal spatial detector 208 behind the object 202, the platform 204 and the driving mechanism for the platform are shown in phantom. Both detectors 206, 208 may be detector arrays. The vertical line detector 206 may comprise two detector arrays 206a, 206b extending from a center 208a of the horizontal detector array 208. At the intersection point between the detector arrays, the vertical line detector 206 can use data from the horizontal spatial detector 208, if necessary. The vertical line detector 206 may be an arc, as can the horizontal detector 208. Rollers 210 are shown on the platform 204 to move the object 202 horizontally. A conveying belt could be used, as well.

To conduct a vertical line scan, a collimator (not shown) that defines a vertical fan beam is moved in front of the source (not shown in this view). The rollers 210 (or belt) may be used to move the object 202 horizontally, completely through the beam. The vertical line detector 206 may comprise a dense array of "deep", high energy conversion detector elements, enabling generation of very high resolution images, as described above. Vertical line scanning may take place either before or after volumetric CT scanning. A vertical line scan may enable identification of items that may be difficult to identify on a volumetric CT image. For example, a detonator and accompanying wires may be more readily identifiable on a line scan. A vertical line scan may optionally be conducted only on suspicious objects or suspicious portions of objects. It is noted that a horizontal line scan could also be conducted based on signals detected by the horizontal detector 208 in this or other embodiments by moving the platform vertically without rotation.

In another alternative, a line scan with the vertical line detector 206 may be performed as described above, and then the platform 204 may be rotated a small amount, such as one degree. The line scan may then repeated. Line scanning and rotation of the platform may be repeated up to 180 degrees, for example, or more. The collected data may then be reconstructed into a volumetric CT image. The volumetric CT images derived from data collected by the one dimensional vertical line detector 206, based on examination with a fan beam, may have different image characteristics than volumetric CT images derived from data detected by the two dimensional horizontal detector 208, based on examination of a rotating and translating object with a cone beam. It may therefore be advantageous to reconstruct volumetric CT images based on data collected by both the horizontal and the vertical detectors 208, 206.

Alternatively, a scanning unit in accordance with another embodiment of the present invention may only include the vertical line detector 206 for reconstruction of volumetric CT imaging without the horizontal line detector 208. While use of such a system may be slower than conducting volumetric CT imaging with a horizontal scanner and both vertical displacement and rotation of the platform 204, it could also be less expensive.

The second source 12*a* in FIG. 1 may also emit a beam of radiation that is collimated into a pencil beam. FIG. 10 is a schematic representation of a portion of a scanning unit 300 including such a source 12*a* and a pencil beam, along with the source 12 that emits a radiation beam that is collimated into a cone beam 80 or a fan beam, as discussed above. A platform 302 supports an object 304. The detector 14 is positioned to receive radiation transmitted through the object 302, as discussed above. A detector 306 is also provided, supported on a rotatable ring 308. The ring 308 is wide enough for the object to be moved through the ring by the vertical movement of the platform 302. The rotatable ring 308 rotates about the same axis "A" that the platform 302 rotates about, to move the detector into a desired position to detect radiation transmitted or scattered by the object 304. The platform may be rotated and moved vertically through the ring 308 by one of the driving mechanisms discussed above, or another such driving mechanism.

If scattered radiation is to be detected, the source 12*a* may emit radiation having a lower energy than if transmitted radiation is to be detected. The source 12*a* may also selectively emit radiation having two or more energies, as discussed above. If it is desired to detect both transmitted and scattered radiation, one of those energies should be high enough to be transmitted through the largest thickness of the object 304 as the object is being rotated. The detector 306 may be moved into alignment with the pencil beam 301 emitted by the source 12*a*, on the opposite side of the object as the source 12*a*, to detect transmitted radiation. The detector 306 may be moved to any desired rotational position around the object by the ring 304, other than in alignment with the pencil beam 301, to detect back scattered, side scattered and/or forward scattered radiation. The ring 308 may support more than one detector, so that radiation may be detected at a plurality of angles at the same time.

Imaging with a pencil beam may be more sensitive to items with certain orientations within the object 304 or smaller items than volumetric CT imaging, but it may be slower. The pencil beam may be used to examine suspicious portions of the object 304 after CT imaging, or the entire object. The energy of the pencil beam and/or the characteristics of the detector 306, as well as the rotational position of the detector, may also be varied to be more sensitive to certain materials. The angle of the pencil beam through the object 302 may be varied, as well. The energy of the pencil beam may be varied to induce scattering due to the atomic structure of the contents, the nuclear structure or the lattice structure (diffraction scattering) of the contents of the object 304.

As mentioned above, since different types of radiation may interact differently with certain materials, providing additional information that may be useful in identifying the contents of the object 304, the source 12*a* of the pencil beam 301 in FIG. 10 need not be a source of X-ray radiation. The source 12*a* may be a source of neutrons, for example. A source of neutrons and/or other types of radiation may be used in the other embodiments of the present invention discussed herein, as well.

The use of high energy X-ray radiation, above about 4 MeV, for example, referred to a gamma rays, as well as neutrons, may induce fission in fissionable material, such as uranium and plutonium, facilitating the identification of nuclear material or devices hidden in the object 304. The detector 306 may be adapted to detect fission byproducts, such as neutrons resulting from pencil beam scanning with gamma rays or X-rays resulting from scanning with neutrons. Fission may be induced with other shaped beams, as well. When inducing radioactivity, however, it may be advantageous to minimize the size of the beam, such as by use of a pencil beam, while maintaining total intensity to improve sensitivity.

Figure 11:
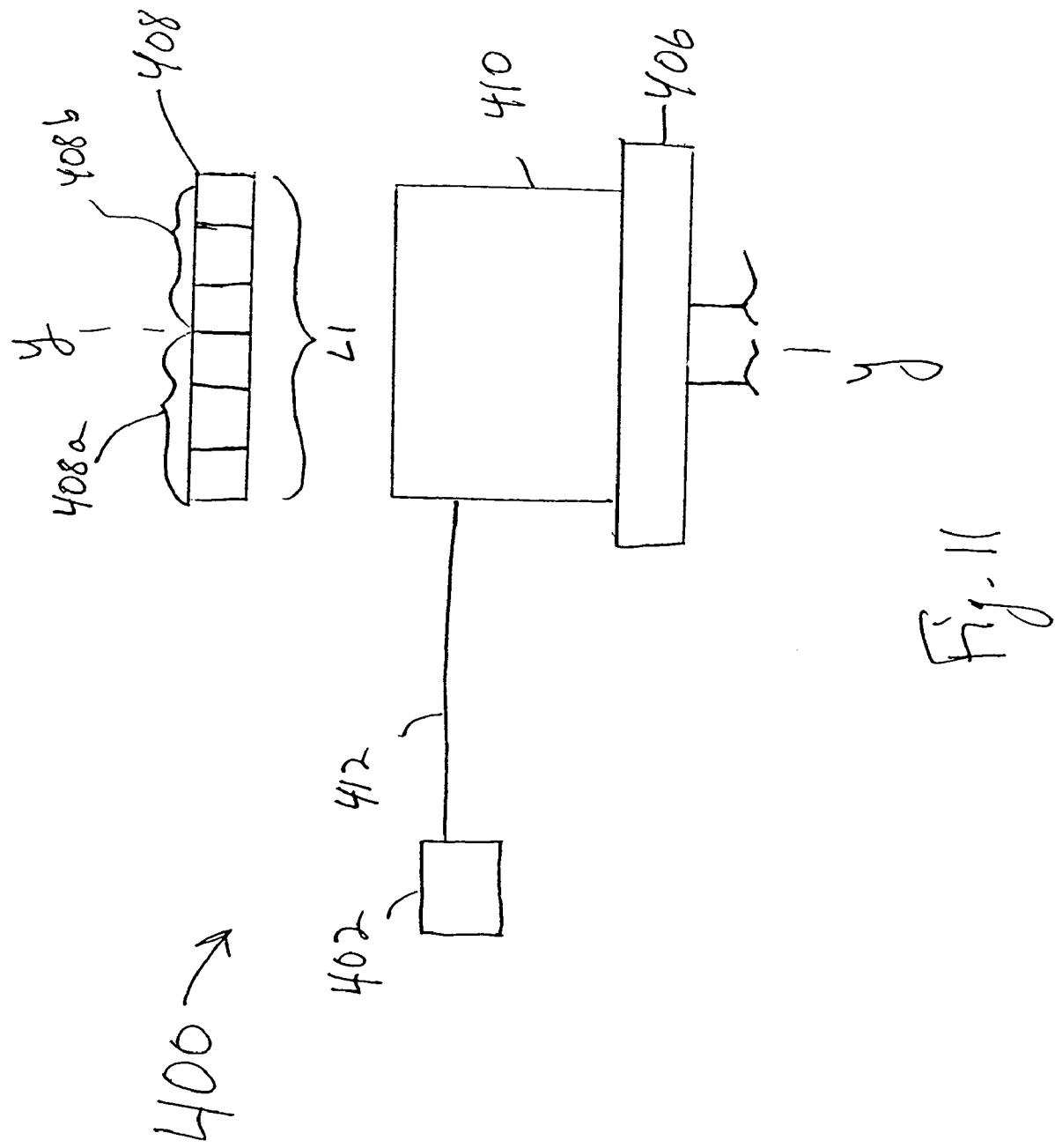
FIG. 11 is a schematic representation of a portion of another scanning unit in accordance with another embodiment, wherein an X-ray source is above an object supported by a rotating/vertically displaceable platform.

FIG. 11 is a schematic representation of a portion of another scanning unit 400 in accordance with another embodiment, particularly suited for detecting stimulated emissions, such as nuclear resonance fluorescence ("NRF"). Scattered radiation may be detected, as well. The scanning unit 400 comprises a radiation source 402, a rotating/vertically displaceable platform 406, as described above, and a detector 408, which may be a detector array, above the platform 406. An object 410 is shown supported by the platform 406. The radiation source 402 may be a source of X-ray radiation, for example. X-ray radiation having an average energy of from about 1 to about 20 MeV or more may be used, dependent upon the species of interest. The detector 408 detects the stimulated emissions and/or scattered radiation caused by the interaction of the radiation with the object. The detector 408 and/or other detectors may also be below the platform 406. The detector may have the shape of an arc, for example. The examination of objects by inducing NRF is discussed in more detail in U.S. Pat. No. 5,420,905 and U.S. Pat. No. 5,115,459, which are incorporated by reference herein.

A collimator (not shown) defines a pencil beam 412 (or other shaped beam) of radiation. The beam 412 has an axis passing through a rotational axis "Y" of the platform 406 and the object 410. The pencil beam may have any desired shape, such as rectangular, square or circular. Any of the conveying systems discussed above, or another type of conveying system, may be provided to move the object 404 to and from the platform 406. The source may be a linear accelerator, such as a Linatron® available from Varian, discussed above.

Figure 12:
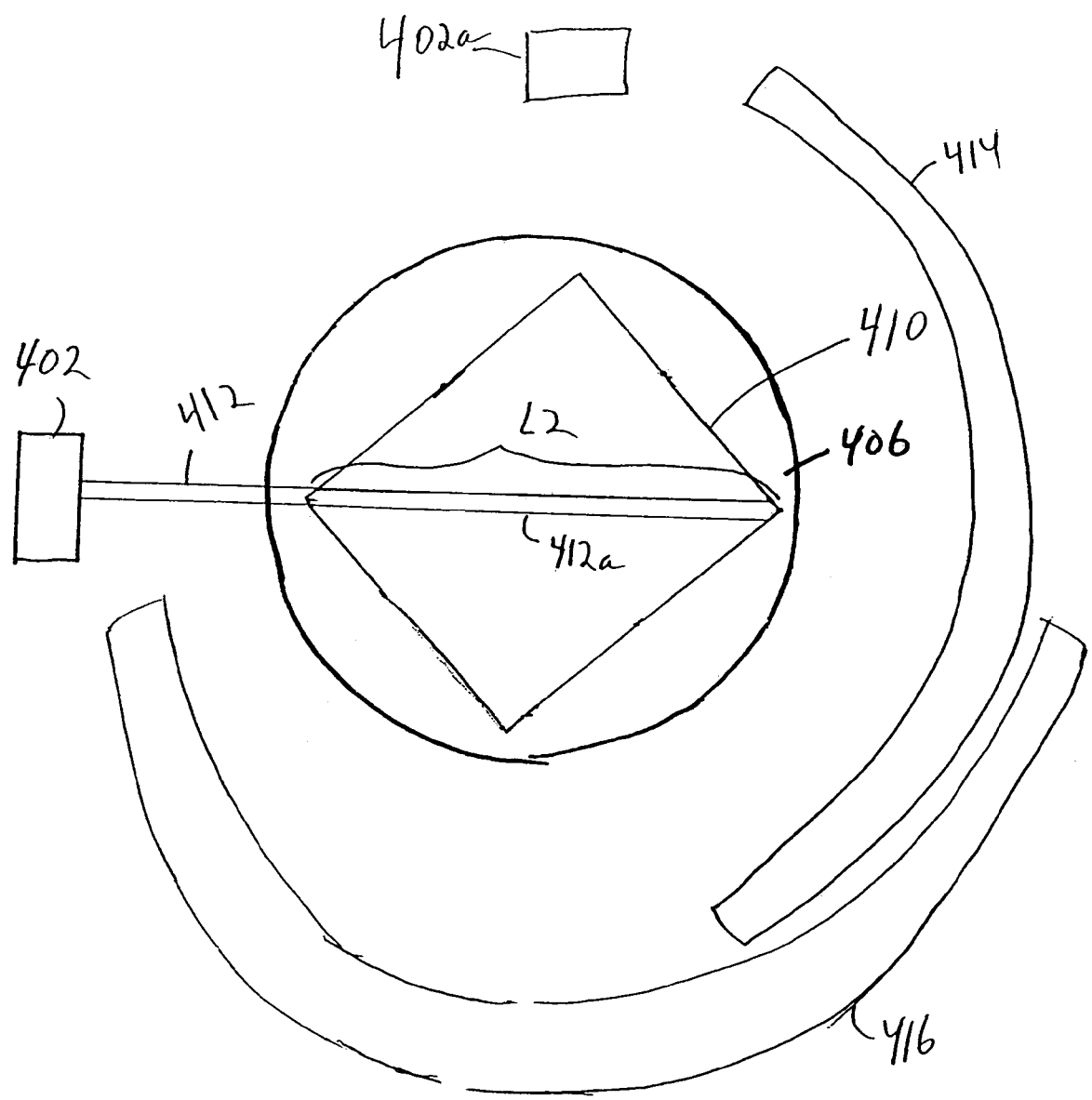
FIG. 12 is a top view of the object on the platform in the embodiment of FIG. 11.

FIG. 12 is a top view of the object 410 on the platform 406, showing the source 402 emitting a pencil beam and a corresponding rectangular diameter 412*a* intercepting the object 404. The width of the pencil beam 412 and the diameter 412*a* are exaggerated in this view. As the platform 406 and the object 404 rotate and move vertically, the rectangular diameter 412*a* sweeps through the object 410. The length "L1" of the detector 408 (see FIG. 11) is preferably at least as long as the length "L2" of the diameter of the object 410 indicated in FIG. 12.

The detector 408 can be an epi-centric NRF detector array, for example. The detector 408 extends at least from the edge of the object 410 to the center of the object. The detector 408 may extend from the center of the object 410 towards the source 402, as indicated by the detector section 408*a*, or away from the source, as indicated by the detector section 408*b*. Preferably, the detector 408 extends a distance equal to the longest diameter of the object as the object is rotated, as shown in the top view of the scanning unit 400 of FIG. 12. If a plurality of detectors in a detector array is provided, different detectors may be optimized to detect different types of NRF gamma rays. NRF emission measurements can be made continuously from the diameter interaction volume as it sweeps through the rotating and vertically moving object 410. Since the detector to probe beam segment distance remains constant, the focusing remains constant. The detector 408 and other detectors, if provided, may be mounted to the ceiling (not shown) of the scanning unit 400.

In this and other embodiments described herein, the generated voxels may be oddly shaped and their size may increase as the distance from the axis of rotation Y of the platform 406 increases. If the probe beam is rectangular, for example, the voxel shape is a three dimensional slanting segment of a rectangular screw thread. The reconstruction algorithm may take this distortion into account, as is known in the art. Since the internal points of the voxels are known in cylindrical coordinates, the display voxels can be reshaped. By comparing voxels on sequential scans, the spatial resolution of the re-shaped voxels may be refined by changing the phase or pitch of the scans, improving spatial resolution by over sampling and non-linear sampling.

If sufficient bremsstrahlung flux is available, a map of the NRF emission may be made in cylindrical coordinates. The NRF cross-sections for various nuclei of interest, and thus the concentrations of those nuclei, can be mapped in the object 410 by Pulse Height Analysis (PHA). The ratios of abundances of various nuclei can be determined in three dimensions for elements, chemical compounds or compositions of compounds and elements.

As mentioned above, for coverage of the entire intersection of the pencil beam with the object 410, there may be a redundancy of epi-centric detectors, before and after the center of rotation and/or above and below the platform 406. This redundancy can be used to optimize the epi-centric detector arrays for multiple ranges of radiation. Individual detector arrays may have differently optimized detectors. This abundance of space for the detection of NRF emission could be very important, since many NRF gamma lines may be analyzed in order to assess various atomic abundances. A database containing information on many NRF gamma lines and many possible ratios of atomic abundance may be used to identify the contents of the object 404. The analysis may be guided by artificial intelligence.

Volumetric CT scanning of the object 410 may also be performed, as discussed above. For example, a second radiation source 402*a* may be provided to emit a horizontally diverging radiation beam, such as a cone beam or a fan beam, as shown in FIG. 12 and discussed above with respect to the embodiment of FIG. 1. A spatial detector 414, which may have an arcuate shape, may be provided to detect radiation interacting with the object, as is also discussed above. The second source 402*a* may be positioned to emit the radiation beam at a right angle, or other large angle, with respect to the pencil beam 412, to avoid detector cross talk and interference due to scatter. Pencil beam pulses 412 may also be strobed with pulses of the horizontal beam. The sources 402 and 402*a* need not be at the same height. Each source 402, 402*a* may emit radiation at the same or different energies, and one or both sources may emit radiation at multiple energies.

Instead of providing a second radiation source 402*a*, the radiation source 402 may also emit a horizontally diverging radiation beam by moving appropriate collimation into position. In that case, a second detector 416 may be used to detect the radiation, as is also shown in FIG. 12. The source 402 may be a multi-energy source. CT may be conducted with an average energy of about 4 MeV for CT and 10 MeV for NRF detection, or about 6 MeV for CT and about 18 MeV for NRF detection, for example.

Images based on the NRF examination of the object 410 and the volumetric CT examination of the object may be separately analyzed. The NRF and CT images may also be readily fused, since the corresponding fusion coordinates are known.

NRF radiation may be detected in the other scanning units described herein by appropriate placement of detectors and selection of scanning energy, as is known in the art.

As mentioned above with respect to the embodiment of FIGS. 11-12, the phase and pitch of the movement of the platform in the embodiments above may be varied to improve resolution and reshape voxels.

While in the preferred embodiments described above the platform rotates about and is translated along a vertical axis, the axis need not be vertical. If the object is adequately secured to the platform, the platform may be rotated about and translated along a non-vertical axis, as well. In addition, the axis of rotation and the axis along which the platform is translated, need not be the same.

Figure 13:
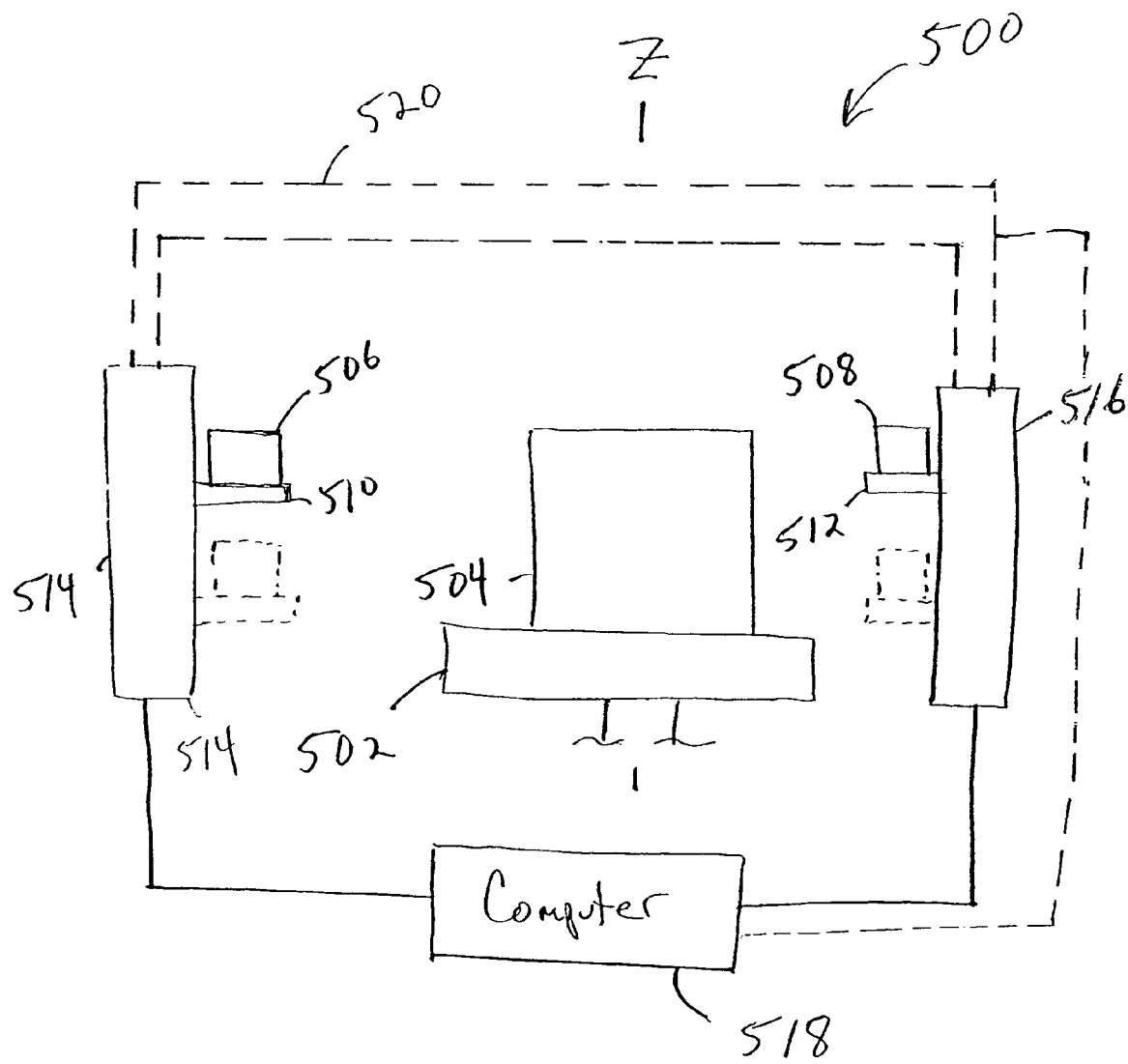
FIG. 13 is a side view of a portion of a scanning unit in accordance with another embodiment of the invention, wherein the source and/or the detector are movable vertically, and a rotatable platform may or may not be movable vertically.

The platform need not be movable vertically or along another axis, to generate volumetric CT images of the object. FIG. 13 is a side view of a portion of a scanning unit 500 in accordance with another embodiment of the invention, wherein a platform 502 supports an object 504. In this embodiment, the platform 502 is rotatable about a vertical axis "Z" but need not be displaceable along that axis or any other axis. Either a radiation source 506 or a detector 508, or both, are displaceable, in this example vertically. The source 506 may emit a radiation beam in the form of a cone beam or a fan beam, for example. The source 506 and the detector 508 may be supported by platforms 510, 512, respectively. The platforms 510, 512 may be vertically displaced upward and downward by units 514, 516, respectively. Appropriate units 514, 516 for moving the platforms 510, 512, include mechanical, electromechanical, hydraulic and pneumatic devices, as is apparent to one skilled in the art. In FIG. 13, second, lower positions of the source 506 and the detector 508 are shown in phantom.

A computer 518, which may be the computer controlling operation of the scanning unit 500, may control the operation of the units 514, 516. As mentioned above, one or the other of the source 506 and the detector 508 may be moved vertically in this example, or both may be moved. If only one or the other is movable vertically, either the source 506 or the detector 508, or both, may be rotated about a horizontal axis to maintain alignment of the radiation beam with the detection plane of the detector. If both the source 506 and the detector 508 are vertically movable, the movement may be synchronized so that the source 506 and the detector 508 stay aligned in the same horizontal plane, as shown in FIG. 13. The motion of the source 506 and detector 508 may be independent, as well. An algorithm may control the movement of the source 506 and detector 508. The platform 502 may also be movable vertically, in conjunction with the vertical movement of the source 506 and/or the detector 508, and its motion may be controlled by an algorithm. The source 506, detector 508 and/or the platform 502 may also be moved along a non-vertical axis.

Volumetric CT images may also be derived if the platform 502 only moves vertically, or in another non-horizontal direction, by moving the source 506 and the detector 508 about the object 504 on the platform. In FIG. 13, the source 506 and the detector 508 are also shown coupled to a rotatable gantry 520 (shown in phantom) to enable rotation of the source and the detector partially or completely about the object 504. The source 502 and/or the detector 508 may be movable with respect to the gantry 520 by the units 514, 516, as well. The detector 508 may also be stationary. In that case, the unit 576 supporting the detector would not be connected to the gantry 520. Rotatable gantries are known in the art. Movement of the gantry 520 may also be controlled by the computer 518.

Cone beam or fan beam reconstruction algorithms may be used to reconstruct volumetric CT images in the embodiments of FIG. 13, as well. Multiple sources, multiple detectors, multiple energies, a pencil beam, and NRF examination, as discussed above, may be used in these embodiments, as well.

One skilled in the art will recognize that other changes may be made to the embodiments described herein without departing from the spirit and scope of the invention, which is defined by the claims, below.

What is claimed is:

1. A scanning unit for inspecting cargo conveyances, comprising:
    a stationary radiation source to emit a beam of radiation, the source being supported at a first level;
    a rotatable platform adapted to support and rotate a cargo conveyance, the platform having a supporting surface to support the cargo conveyance for inspection by the beam of radiation, the platform being rotatable about a substantially vertical axis substantially perpendicular to the supporting surface; and
    a stationary detector positioned to receive radiation transmitted through the cargo conveyance, the stationary detector being supported at a second level;
    wherein the platform is movable along the substantially vertical axis during rotation of the platform, the platform being movable at least partially within a cavity defined below at least one of the first or second levels; and
    the source and the detector are positioned to allow the cargo conveyance to pass therebetween, during operation;
    the unit further comprising:
    at least one processor configured to reconstruct helical computed tomographic images of at least a portion of the cargo conveyance, during operation.

2. The scanning unit of claim 1, wherein the source is a source of X-ray radiation.

3. The scanning unit of claim 1, wherein the detector is a detector array.

4. The scanning unit of claim 1, wherein the detector is aligned with the source.

5. The scanning unit of claim 1, further comprising means for rotating the platform and moving the platform along the substantially vertical axis.

6. The scanning unit of claim 5, wherein the means synchronously rotates and moves the platform.

7. The scanning unit of claim 1, wherein the first direction is substantially vertical, the scanning unit further comprising:
    a screw jack coupled to the platform to rotate the platform and move the platform along the substantially vertical axis.

8. The scanning unit of claim 7, wherein rotation of the screw jack causes rotation of the platform in a single rotational direction as the platform is moved upward and vertically along the substantially vertical axis.

9. The scanning unit of claim 1, further comprising:
    a motor coupled to the platform to rotate the platform; and
    a pneumatic or hydraulic device coupled to the platform to cause movement of the platform along the substantially vertical axis.

10. The scanning unit of claim 1, further comprising a first conveyor to convey the cargo conveyance to the platform for scanning.

11. The scanning unit of claim 10, wherein the first conveyor is configured to convey the cargo conveyance away from the platform after scanning.

12. The scanning unit of claim 10, further comprising a second conveyor to convey the cargo conveyance from the platform after scanning.

13. The scanning unit of claim 1, wherein the beam is a cone beam or a fan beam.

14. The scanning unit of claim 1, wherein the beam is a cone beam and the detector comprises a detector array comprising a plurality of two dimensional detectors.

15. The scanning unit of claim 1, further comprising a second radiation source to emit a radiation beam;
    wherein the first radiation source emits a radiation beam having a first energy distribution and the second radiation source emits a radiation beam having a second energy distribution different than the first energy distribution.

16. The scanning unit of claim 15, wherein the first energy distribution has a peak in the MeV range and the second energy distribution has a peak in the KeV range.

17. The scanning unit of claim 1, further comprising a second, energy sensitive, detector,
    wherein the first detector is between the second detector and the radiation source.

18. The scanning unit of claim 17, wherein the at least one processor is electrically coupled to the second detector, the at least one processor being further configured to:
    reconstruct energy based images based on data received from the second detector; and
    fuse the images based on data from the first detector with the images based on the data received from the second detector.

19. The scanning unit of claim 1, wherein the radiation source is operational to be selectively switched between emitting a radiation beam having a first energy distribution and a radiation beam having a second energy distribution different than the first energy distribution.

20. The scanning unit of claim 1, wherein:
    the beam is a horizontally extending beam; and
    the detector extends horizontally.

21. The scanning unit of claim 20, further comprising:
    a second radiation source to emit a vertically extending beam; and
    a vertically extending detector to receive radiation after interaction of the vertically extending beam with the object.

22. The scanning unit of claim 1, further comprising:
    a second radiation source to emit a pencil beam of radiation; and
    a second detector to receive radiation after interaction of the pencil beam with the object.

23. The scanning unit of claim 1, further comprising:
    a second detector positioned to detect stimulated emissions.

24. The scanning unit of claim 23, further comprising:
a second source of radiation to emit a pencil beam along a first axis;
wherein:
the stimulated emissions are nuclear resonance fluorescence; and
the second detector is positioned to detect nuclear resonance fluorescence emitted substantially perpendicular to the first axis of the pencil beam.

25. The scanning unit of claim 1, further comprising:
at least one second radiation source to emit a beam of radiation;
wherein:
the stationary radiation source is a source of X-ray radiation; and
the second radiation source is a source of a type of radiation different than X-ray radiation.

26. The scanning unit of claim 1, wherein the cargo conveyance is at least about 6 feet wide.

27. The scanning unit of claim 26, wherein the stationary source is adapted to emit radiation having an energy distribution with a peak in the MeV range.

28. The scanning unit of claim 1, wherein the detector array comprises:
spatial detector elements; and
energy sensitive detector elements.

29. The scanning unit of claim 1, wherein the first level and the second level are the same.

30. The scanning unit of claim 1, wherein the cavity is defined, at least in part, by ground.

31. A scanning unit for inspecting objects, comprising:
at least one source of penetrating radiation to emit a beam of radiation to scan an object;
a platform to support an object during scanning by the beam of radiation, the platform being rotatable about an axis and movable along the axis;
at least one detector positioned to receive radiation after interaction with the object;
a first conveyor to convey the object to the platform for scanning;
a second conveyor to convey the object from the platform after scanning, the second conveyor being at a first vertical height; and
a third conveyor to convey the object from the platform after scanning, the third conveyor being at a second vertical height different than the first vertical height;
wherein the platform is configured to selectively direct the object to one of the second conveyor and the third conveyor by moving the platform along the axis, between the first height and the second height.

32. The scanning unit of claim 31, further comprising a processor configured to cause movement of the platform between the first height and second height to align the object with the second conveyor if the object passes inspection and to align the object with the third conveyor if the object has not passed inspection.

33. The scanning unit of claim 31, further comprising:
a fourth conveyor to selectively convey the object from the platform after scanning and return the object to the platform for rescanning;
wherein the platform is rotatably positionable to selectively align the object with one of the second conveyor and the fourth conveyor.

34. The scanning unit of claim 33, wherein the second conveyor and the fourth conveyor are at the first vertical height.

35. The scanning unit of claim 31, further comprising a fourth conveyor on the platform to move the object during scanning.

36. The scanning unit of claim 31, wherein:
the platform is configured to support a cargo conveyance; and
the source and the detector are configured to scan a cargo conveyance.

37. The scanning unit of claim 31, wherein the penetrating radiation comprises X-ray radiation.

38. A scanning unit for inspecting objects, comprising:
at least one radiation source configurable to emit a vertical beam of radiation;
a platform rotatable about a vertical axis to support an object for inspection by the vertical beam of radiation;
a conveyor on the platform to move the object horizontally during scanning by the vertical beam; and
a vertical detector aligned with the vertical beam, to receive radiation after interaction with the object.

39. The scanning unit of claim 38, wherein the vertical beam is a fan beam.

40. The scanning unit of claim 38, wherein:
the platform is vertically displaceable; and
at least one of the at least one sources is configurable to emit a second, horizontal beam of radiation; and
the scanning unit further comprises:
a second horizontal detector positioned to receive radiation from the interaction of the horizontal beam with the object; and
a processor coupled to the second detector, the processor being configured to reconstruct computed tomographic images based, at least in part, on radiation received by the second detector.

41. The scanning unit of claim 40, wherein the first source and the second source are the same.

42. The scanning unit of claim 40, wherein the first radiation beam is a fan beam and the second radiation beam is one of a cone beam and a fan beam.

43. The scanning unit of claim 40, wherein:
the first detector and the second detector intersect to form a cross.

44. The scanning unit of claim 38, further comprising:
a processor coupled to the first detector, the processor being configured to reconstruct computed tomographic images based, at least in part, on radiation detected by the first detector.

45. A scanning unit for inspecting objects, comprising:
a first radiation source to emit a pencil beam of radiation;
a rotatable platform to support an object for inspection by the beam of radiation; and
a detector positioned to receive radiation after interaction with the object;
wherein:
at least one of the radiation source, the detector or the platform is vertically displaceable;
the scanning unit further comprising:
a second radiation source of a horizontal beam of X-ray radiation; and
a second, horizontally extending detector aligned with the second source to receive radiation after interaction of the horizontal beam with the object.

46. The scanning unit of claim 45, wherein the first detector is movable to receive radiation scattered by the object along a predetermined direction.

47. The scanning unit of claim 46, wherein the first detector is supported on a rotatable ring with an axis of rotation transverse to the platform.

48. The scanning unit of claim 45, wherein the first detector is adapted to detect fission byproducts.

49. The scanning unit of claim 48, wherein the first radiation source is a source of one of neutrons and gamma rays.

50. The scanning unit of claim 45, wherein the first source of the pencil beam and the second source of the horizontally extending beam are the same.

51. A scanning unit for inspecting objects, comprising:
at least one stationary radiation source to emit beams of radiation at at least first and second, different, energy distributions;
a platform to support an object for inspection by the beams of radiation, the platform being rotatable about an axis and displaceable along the axis, wherein the platform is configured to simultaneously rotate and be displaced during scanning;
a stationary detector positioned to receive radiation after interaction of the beam with the object; and
a processor configured to cause emission of a radiation beam from the at least one stationary radiation source having the first energy distribution while the platform is being displaced in a first direction along the axis and to cause emission of a radiation beam from the at least one stationary radiation source having the second energy distribution while the platform is being displaced in a second, different direction along the axis.

52. The scanning unit of claim 51 wherein the axis is a vertical axis.

53. A method of examining contents of a cargo conveyance comprising:
rotating the cargo conveyance about a substantially vertical axis of rotation;
moving the cargo conveyance along the substantially vertical axis of rotation, while rotating the cargo conveyance;
scanning the cargo conveyance with radiation from a stationary radiation source while rotating the cargo conveyance and moving the cargo conveyance;
detecting radiation transmitted through the cargo conveyance with a first, stationary spatial detector;
detecting radiation transmitted through the cargo conveyance with a second stationary energy sensitive, detector;
reconstructing volumetric computed tomography images from the radiation detected by the first detector;
reconstructing images from the radiation detected by the second detector; and
fusing corresponding images from the radiation detected from the first and second detectors.

54. The method of claim 53, comprising scanning the cargo conveyance while rotating the cargo conveyance and moving the cargo conveyance in the first direction.

55. The method of claim 53, comprising scanning the cargo conveyance with one of a cone beam and a fan beam of radiation.

56. The method of claim 53, comprising scanning the cargo conveyance with X-ray radiation.

57. The method of claim 56, comprising scanning the cargo conveyance with a radiation beam having a first energy distribution and scanning the cargo conveyance with a radiation beam having a second energy distribution different from the first energy distribution.

58. The method of claim 53, further comprising:
moving the cargo conveyance horizontally;
scanning the cargo conveyance with a vertical beam of radiation; and
detecting radiation from the interaction of the vertical beam with the cargo conveyance with a vertical detector.

59. The method of claim 53, comprising:
scanning the cargo conveyance with radiation to induce fission in fissionable material in the object, if present; and
detecting fission byproducts.

60. The method of claim 59, comprising scanning the cargo conveyance with a pencil beam of neutron or gamma ray radiation.

61. The method of claim 53, further comprising conveying the cargo conveyance from the platform along one of a plurality of exit paths based, at least in part, on one of a rotational position and a vertical position of the platform.

62. The method of claim 53, comprising detecting stimulated emissions from the cargo conveyance.

63. The method of claim 62, comprising detecting nuclear resonance fluorescence radiation from the cargo conveyance.

64. The method of claim 53, comprising:
scanning the cargo conveyance while the cargo conveyance is being moved in a first vertical direction; and
scanning the cargo conveyance while the cargo conveyance is being moved in a second vertical direction, opposite the first direction.

65. The method of claim 53, comprising moving the cargo conveyance vertically.

66. The method of claim 53, wherein the cargo conveyance has a length greater than a width, the method further comprising:
orienting the cargo conveyance so that the length is aligned with the vertical axis.

67. A method of examining contents of an object, comprising:
rotating the object about an axis of rotation;
moving the object along a direction of the axis of rotation;
scanning at least a portion of the object with radiation having a first energy distribution;
detecting radiation at the first energy distribution interacting with the object, by a spatial detector;
scanning at least a portion of the object with radiation having a second energy distribution;
detecting radiation at the second energy distribution interacting with the object, by an energy detector;
combining a function of the first detected radiation with a function of the second detected radiation; and
analyzing the combined function.

68. The method of claim 67, comprising analyzing the combined function by:
reconstructing at least one image based, at least in part, on the combined function; and
analyzing the at least one image.

69. A method of examining contents of an object, comprising:
rotating the object about an axis;
moving the object along the axis in a first direction;
scanning the object with X-ray radiation at a first energy distribution while the object is being moved along the axis in the first direction;
moving the object along the axis in a second direction opposite to the first direction;
scanning the object with X-ray radiation having a second energy distribution different from the first energy distribution while the object is being moved along the axis in the second direction; and
detecting radiation interacting with the object.

70. The method of claim 69, further comprising:
simultaneously rotating the object, scanning the object and moving the object; and
reconstructing helical computed tomographic images based, at least in part, on the detected radiation.

71. A scanning unit for inspecting objects, comprising:
a radiation source to emit a pencil beam of radiation, along a first axis;
a rotatable platform to support an object for inspection by the beam of radiation, the platform being rotatable about an axis; and
a detector configured and positioned to receive nuclear resonance fluorescence emitted from the object substantially perpendicular to an axis of the pencil beam, due to interaction of the beam with the object;
wherein at least one of the radiation source, the detector or the platform is movable along a direction of the axis.

72. The scanning unit of claim 71, further comprising:
a second radiation source to emit a second beam of radiation; and
a second detector aligned with the second radiation source to receive radiation after interaction of the second beam with the object;
wherein at least one of the second radiation source, the platform or the second detector is movable in the first direction.

73. The scanning unit of claim 72, further comprising:
a processor coupled to the second detector, the processor being configured to generate computed tomographic images based, at least in part, on radiation received by the second detector.

74. A method of examining contents of an object, comprising:
scanning an object with a radiation beam;
detecting radiation transmitted through the object with a first, spatial detector;
detecting radiation transmitted through the object and the first detector with a second, energy sensitive, detector behind the first detector;
reconstructing first computed tomographic images from radiation detected by the first detector;
reconstructing second images from radiation detected by the second detector; and
fusing corresponding first and second images.

75. A scanning unit for inspecting objects, the unit comprising:
a radiation source to emit a beam of neutrons;
a rotatable platform adapted to support and rotate a an object, the platform having a supporting surface to support the object for inspection by the beam of radiation, the platform being rotatable about an axis substantially perpendicular to the supporting surface;
a detector positioned to receive radiation transmitted through the object;
a conveyor adapted to convey the object to the platform for scanning; and
at least one processor configured to reconstruct helical computed tomographic images of at least a portion of the object, during operation;
wherein at least one of the radiation source, the platform or the detector is movable in a direction along a direction of the axis during rotation of the platform.

76. A scanning unit for inspecting objects, comprising:
a first radiation source to emit a radiation beam having a first energy distribution;
a second radiation source to emit a radiation beam having a second energy distribution different than the first energy distribution;
a rotatable platform having a supporting surface to support an object for inspection by the beam of radiation, the platform being rotatable about an axis substantially perpendicular to the supporting surface; and
a detector positioned to receive radiation after interaction of the beam with the object; and
at least one processor configured to:
reconstruct first computed tomographic images of at least a portion of the object based, at least in part, on radiation detected at the first energy distribution, during operation; and
reconstruct second computed tomographic images of at least a portion of the object based, at least in part, on radiation detected at the second energy distribution, during operation;
wherein at least one of the first and second radiation sources, the platform or the detector is movable in a direction along a direction of the axis during rotation of the platform.

77. The scanning unit of claim 76, wherein the processor is further configured to:
fuse corresponding first and second reconstructed images.

78. A method of examining contents of an object, comprising:
rotating the object about an axis;
scanning the object with a radiation beam from at least one radiation source having a first energy distribution;
scanning the object with a radiation beam from the at least one radiation source having a second energy distribution different from the first energy distribution;
detecting radiation interacting with the object by a detector;
moving at least one of the object, the at least one radiation source or the detector along the axis of rotation; and
reconstructing at least one first helical computed tomographic image based, at least in part, on the detected radiation at the first energy distribution; and
reconstructing at least one second helical computed tomographic image based, at least in part, on the detected radiation at the second energy distribution.

79. The method of claim 78, further comprising:
fusing corresponding first and second reconstructed images.

80. A method of examining contents of an object, comprising:
rotating the object about an axis of rotation;
moving at least one of the object, a radiation source or a detector along the axis of rotation, while rotating the object;
scanning the object with radiation from the radiation source to induce fission in fissionable material in the object, if present, while rotating the object and moving at least one of the object, the radiation source or the detector; and
detecting fission byproducts.

81. The method of claim 80, comprising scanning the cargo conveyance with a pencil beam of neutron or gamma ray radiation.

82. A scanning unit for inspecting objects, comprising:
a radiation source to emit a beam of radiation;
a rotatable platform having a supporting surface to support an object for inspection by the beam of radiation, the platform being rotatable about an axis substantially perpendicular to the supporting surface;

a first, energy sensitive detector;
a second detector positioned to receive radiation after interaction of the beam with the object, the second detector being between the first detector and the radiation source; and
at least one processor configured to:
reconstruct at least one first computed tomographic image of at least a portion of the object, during operation, based, at least in part, on the detected radiation from the first, energy sensitive detector;
reconstruct at least one second image of at least a the portion of the object, during operation, based, at least in part, on the detected radiation from the second detector; and
fuse at least certain of the first and second images;
wherein at least one of the radiation source, the platform or the detector is movable in a direction along a direction of the axis.

83. A scanning unit for inspecting objects, comprising:
a radiation source to emit a beam of radiation, the radiation source being operational to be selectively switched between emitting a radiation beam having a first energy distribution and a radiation beam having a second energy distribution different than the first energy distribution;
a rotatable platform having a supporting surface to support an object for inspection by the beam of radiation, the platform being rotatable about an axis substantially perpendicular to the supporting surface;
a detector positioned to receive radiation after interaction of the beam with the object; and
at least one processor configured to reconstruct at least one helical computed tomographic image based, at least in part, on the detected radiation;
wherein at least one of the radiation source, the platform or the detector is movable in a direction along a direction of the axis.

84. A method of examining contents of an object, comprising:
rotating an object about a first axis;
moving the object along the axis;
conducting a first radiation scan of the object with penetrating radiation;
changing a scanning parameter;
conducting a second radiation scan of the object with penetrating radiation after changing the scanning parameter;
detecting radiation interacting with the object; and
reconstructing at least one computed tomographic image based on the detected radiation prior to changing the scanning parameter; and
reconstructing at least one computed tomographic image based on the detected radiation after changing the scanning parameter.

85. The method of claim 84, wherein the scanning parameter comprises rotation speed, the method comprising:
scanning at least a portion of the object while rotating the object at a first speed; and
scanning at least a portion of the object while rotating the object at a second speed different than the first speed.

86. The method of claim 84, wherein the scanning parameter comprises movement speed along the axis, the method further comprising:
scanning at least a portion of the object while moving the object along the axis at a first speed; and
scanning at least a portion of the object while moving the object along the axis at a second speed different than the first speed.

87. The method of claim 84, wherein the scanning parameter comprises dose rate, the method further comprising:
scanning at least a portion of the object at a first dose rate; and
scanning at least a portion of the object at a second dose rate different than the first dose rate.

88. The method of claim 84, comprising:
conducting the first radiation scan while rotating and/or moving the object.

89. A scanning unit for inspecting objects, comprising:
at least one source of penetrating radiation to emit a beam of radiation to scan an object;
a platform to support an object during scanning by the beam of radiation, the platform being movable along an axis;
at least one detector positioned to receive radiation after interaction with the object;
a first conveyor to convey the object to the platform for scanning;
a second conveyor to convey the object from the platform after scanning, the second conveyor being at a first vertical height; and
a third conveyor to convey the object from the platform after scanning, the third conveyor being at a second vertical height different than the first vertical height;
wherein the platform is configured to selectively direct the object to one of the second conveyor and the third conveyor by moving the platform along the axis, between the first height and the second height.

90. A scanning unit for inspecting objects, comprising:
at least one radiation source to emit beams of radiation at at least first and second, different, energy distributions;
a platform to support an object for inspection by the beams of radiation, the platform being movable along an axis;
a detector positioned to receive radiation after interaction of the beam with the object; and
a processor configured to cause emission of a radiation beam from the at least one radiation source having the first energy distribution while the platform is moved in a first direction along the axis and to cause emission of a radiation beam from the at least one radiation source having the second energy distribution while the platform is moved in a second, different direction along the axis.

91. A method of examining contents of a cargo conveyance comprising:
rotating the cargo conveyance about a substantially vertical axis of rotation;
moving the cargo conveyance along the substantially vertical axis of rotation, while rotating the cargo conveyance;
scanning the cargo conveyance with radiation from a stationary radiation source while rotating the cargo conveyance and moving the cargo conveyance;
detecting radiation transmitted through the cargo conveyance by a stationary detector;
reconstructing at least one helical computed tomographic image based, at least in part, on the detected radiation
scanning the cargo conveyance with radiation to induce fission in fissionable material in the object, if present; and
detecting fission byproducts.

* * * * *